(12) United States Patent
Amoroso et al.

(10) Patent No.: US 9,421,307 B2
(45) Date of Patent: Aug. 23, 2016

(54) BIOHYBRID COMPOSITE SCAFFOLD

(75) Inventors: Nicholas J. Amoroso, Pittsburgh, PA (US); Stephen F. Badylak, Pittsburgh, PA (US); Yi Hong, Pittsburgh, PA (US); Alexander Huber, Pittsburgh, PA (US); Keisuke Takanari, Pittsburgh, PA (US); William R. Wagner, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 583 days.

(21) Appl. No.: 13/814,783

(22) PCT Filed: Aug. 17, 2011

(86) PCT No.: PCT/US2011/048071
§ 371 (c)(1),
(2), (4) Date: Jun. 18, 2013

(87) PCT Pub. No.: WO2012/024390
PCT Pub. Date: Feb. 23, 2012

(65) Prior Publication Data
US 2013/0253663 A1    Sep. 26, 2013

Related U.S. Application Data

(60) Provisional application No. 61/374,340, filed on Aug. 17, 2010.

(51) Int. Cl.
*A61L 27/58* (2006.01)
*A61L 27/36* (2006.01)
*A61L 27/18* (2006.01)
*A61L 27/48* (2006.01)

(52) U.S. Cl.
CPC ............. *A61L 27/58* (2013.01); *A61L 27/18* (2013.01); *A61L 27/3633* (2013.01); *A61L 27/48* (2013.01)

(58) Field of Classification Search
None
See application file for complete search history.

(56) References Cited

U.S. PATENT DOCUMENTS

| | | | |
|---|---|---|---|
| 4,902,508 A | 2/1990 | Badylak et al. |
| 4,956,178 A | 9/1990 | Badylak et al. |
| 4,970,298 A | 11/1990 | Silver et al. |
| 5,053,228 A | 10/1991 | Mori et al. |
| 5,124,421 A | 6/1992 | Ulbrich et al. |
| 5,171,262 A | 12/1992 | MacGregor |
| 5,275,826 A | 1/1994 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,516,533 A | 5/1996 | Badylak et al. |
| 5,554,389 A | 9/1996 | Badylak et al. |
| 5,573,784 A | 11/1996 | Badylak et al. |
| 5,610,241 A | 3/1997 | Lee et al. |
| 5,645,860 A | 7/1997 | Knapp, Jr. et al. |
| 5,665,391 A | 9/1997 | Lea |
| 5,702,717 A | 12/1997 | Cha et al. |
| 5,711,969 A | 1/1998 | Patel et al. |
| 5,741,701 A | 4/1998 | Swiderek et al. |
| 5,753,267 A | 5/1998 | Badylak et al. |
| 5,762,966 A | 6/1998 | Knapp, Jr. et al. |
| 5,807,581 A | 9/1998 | Rosenblatt et al. |
| 5,866,414 A | 2/1999 | Badylak et al. |
| 5,885,619 A | 3/1999 | Patel et al. |
| 5,955,110 A | 9/1999 | Patel et al. |
| 5,968,096 A | 10/1999 | Whitson et al. |
| 6,030,634 A | 2/2000 | Wu et al. |
| 6,099,567 A | 8/2000 | Badylak et al. |
| 6,187,039 B1 | 2/2001 | Hiles et al. |
| 6,264,992 B1 | 7/2001 | Voytik-Harbin et al. |
| 6,444,229 B2 | 9/2002 | Voytik-Harbin et al. |
| 6,458,889 B1 | 10/2002 | Trollsas et al. |
| 6,485,723 B1 | 11/2002 | Badylak et al. |
| 6,551,618 B2 | 4/2003 | Baird et al. |
| 6,554,857 B1 | 4/2003 | Zilla et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,833,408 B2 | 12/2004 | Sehl et al. |
| 6,841,617 B2 | 1/2005 | Jeong et al. |
| 6,849,273 B2 | 2/2005 | Spievack |
| 6,852,339 B2 | 2/2005 | Spievack |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 6,979,464 B2 | 12/2005 | Gutowska |

(Continued)

FOREIGN PATENT DOCUMENTS

| | | |
|---|---|---|
| WO | 2004014969 A1 | 2/2004 |
| WO | 2010096795 A1 | 8/2010 |

OTHER PUBLICATIONS

Ekaputra et al, Biomacromolecules, 2008, vol. 9, pp. 2097-2103.*
Hashizume et al, Biomaterials, 2010, vol. 31, p. 3253-3265.*
Hong et al, Biomaterials, 2011, vol. 32, pp. 3387-3394.*
Stankus et al, J Biomed Mater Res A, 2004, vol. 70, No. 4, pp. 603-614.*
Stankus et al, J Biomater Sci, Polymer Ed, 2008, vol. 19, No. 5, pp. 635-652.*

(Continued)

*Primary Examiner* — Allison Fox
(74) *Attorney, Agent, or Firm* — The Webb Law Firm

(57) ABSTRACT

A biohybrid scaffold is provided that is useful in clinical applications for abdominal wall reconstruction, pelvic floor repair, breast reconstruction, as well as other soft tissue repairs. Methods of making and using the biohybrid scaffold are provided.

16 Claims, 27 Drawing Sheets

(56) References Cited

U.S. PATENT DOCUMENTS

| | | |
|---|---|---|
| 7,094,418 B2 | 8/2006 | Chudzik et al. |
| 7,235,295 B2 | 6/2007 | Laurencin et al. |
| 7,374,774 B2 | 5/2008 | Bowlin et al. |
| 7,569,233 B2 | 8/2009 | Malaviya et al. |
| 8,053,559 B2 | 11/2011 | Nielsen et al. |
| 8,267,960 B2 | 9/2012 | Argenta et al. |
| 8,361,503 B2 | 1/2013 | Badylak et al. |
| 2001/0014475 A1 | 8/2001 | Frondoza et al. |
| 2002/0015734 A1 | 2/2002 | Uludag et al. |
| 2002/0081732 A1 | 6/2002 | Bowlin et al. |
| 2002/0085994 A1 | 7/2002 | Ceres et al. |
| 2002/0090725 A1 | 7/2002 | Simpson et al. |
| 2003/0012822 A1 | 1/2003 | Voytik-Harbin et al. |
| 2003/0021827 A1 | 1/2003 | Malaviya et al. |
| 2003/0100944 A1 | 5/2003 | Laksin et al. |
| 2004/0001892 A1 | 1/2004 | Healy et al. |
| 2004/0009600 A1 | 1/2004 | Bowlin et al. |
| 2005/0181016 A1 | 8/2005 | Freyman et al. |
| 2005/0238722 A1 | 10/2005 | Pathak et al. |
| 2005/0260179 A1 | 11/2005 | Fishman et al. |
| 2006/0034889 A1 | 2/2006 | Jo et al. |
| 2006/0085063 A1 | 4/2006 | Shastri et al. |
| 2006/0134079 A1 | 6/2006 | Sih et al. |
| 2006/0147433 A1 | 7/2006 | Hiles |
| 2006/0149309 A1 | 7/2006 | Paul et al. |
| 2006/0257377 A1 | 11/2006 | Atala et al. |
| 2007/0014755 A1 | 1/2007 | Beckman et al. |
| 2007/0014773 A1 | 1/2007 | Matheny et al. |
| 2007/0014870 A1 | 1/2007 | Matheny |
| 2007/0014871 A1 | 1/2007 | Matheny |
| 2007/0014872 A1 | 1/2007 | Matheny et al. |
| 2007/0014873 A1 | 1/2007 | Matheny |
| 2007/0014874 A1 | 1/2007 | Matheny |
| 2007/0207186 A1 | 9/2007 | Scanlon et al. |
| 2007/0225631 A1 | 9/2007 | Bowlin et al. |
| 2007/0275458 A1 | 11/2007 | Gouma |
| 2008/0009830 A1 | 1/2008 | Fujimoto et al. |
| 2008/0096975 A1 | 4/2008 | Guan et al. |
| 2008/0109070 A1 | 5/2008 | Wagner et al. |
| 2008/0159985 A1 | 7/2008 | Bowlin et al. |
| 2008/0208323 A1 | 8/2008 | El-Kurdi et al. |
| 2008/0213389 A1 | 9/2008 | Lelkes et al. |
| 2008/0260831 A1 | 10/2008 | Badylak et al. |
| 2008/0268019 A1 | 10/2008 | Badylak et al. |
| 2010/0222882 A1 | 9/2010 | Badylak et al. |

OTHER PUBLICATIONS

Au et al., Thermally reversible polymer gel for chondrocyte culture, J Biomed Mater Res A, Dec. 2003, pp. 1310-1319, vol. 67, No. 4.
Badylak et al., Esophageal Reconstruction with ECM and Muscle Tissue in a Dog Model, Journal of Surgical Research, Sep. 2005, pp. 87-97, vol. 128, No. 1.
Badylak et al., Extracellular Matrix for Myocardial Repair, Heart Surgery Forum, 2003, pp. E20-E26, vol. 6, No. 2.
Badylak et al., Naturally Occurring Extracellular Matrix as a Scaffold for Musculoskeletal Repair, Clinical Orthophaedics and Related Research, Oct. 1999, pp. S333-S343, No. 367S.
Badylak et al., Resorbable Bioscaffold for Esophageal Repair in a Dog Model, Journal of Pediatric Surgery, Jul. 2000, pp. 1097-1103, vol. 35, No. 7.
Badylak, The extracellular matrix as a scaffold for tissue reconstruction, Seminars in Cell & Developmental Biology, 2002, pp. 377-383, vol. 13.
Badylak et al., The Use of Extracellular Matrix as an Inductive Scaffold for the Partial Replacement of Functional Myocardium, Cell Transplantation, 2006, pp. S29-S40, vol. 15., Supplement 1.
Badylak et al., The use of xenogenic small intestinal submucosa as a biomaterial for Achille's tendon repair in a dog model, Journal of Biomedical Materials Research, Aug. 1995, pp. 977-985, vol. 29, No. 8.
Badylak, Xenogenic extracellular matrix as a scaffold for tissue reconstruction, Transplant Immunology, 2004, pp. 367-377, vol. 12.

Bernacca et al., Polyurethane heart valve durability: effects of leaflet thickness and material, International Journal of Artificial Organs., Jun. 1997, pp. 327-331, vol. 20, No. 6.
Billiar et al., Biaxial Mechanical Properties of the Natural and Glutaraldehyde Treated Aortic Valve Cusp—Part I: Experimental Results, Journal of Biomechanical Engineering, Feb. 2000, pp. 23-30, vol. 122, No. 1.
Brightman et al., Time-Lapse Confocal Reflection Microscopy of Collagen Fibrillogenesis and Extracellular Matrix Assembly In Vitro, Biopolymers, Sep. 2000, pp. 222-234, vol. 54, No. 3.
Bromberg et al., Temperature-responsive gels and thermogelling polymer matrices for protein and peptide delivery, Advanced Drug Delivery Reviews, May 1998, pp. 197-221, vol. 31, No. 3.
Cao et al., Preparation and Use of Thermosensitive Polymers, Methods in Molecular Medicine, vol. 18: Tissue Engineering Methods and Protocols, 1999, pp. 75-84, Humana Press Inc., Totowa, NJ.
Chaudhuri et al., Detection and gradation of oriented texture, Pattern Recognition Letters, Feb. 1993, pp. 147-153, vol. 14, No. 2.
Cho et al., Chondrogenic differentiation of human mesenchymal stem cells using a thermosensitive poly(N-isoproplyacrylamide) and water-soluble chitosan copolymer, Biomaterials, Nov. 2004, pp. 5743-5751, vol. 25, No. 26.
Courtney et al., Analysis and design of novel electrospun PEUU scaffolds for soft tissue engineering, ASME Jun. 2005 Summer Bioengineering Conference, Jun. 22-26, 2005, Abstract # b0241329, 1 page.
Courtney et al., Analysis and design of novel electrospun PEUU scaffolds for soft tissue engineering, The 8th Annual Meeting of the Tissue Engineering Society International, Oct. 22-25, 2005, Abstract # 193, 1 page.
Courtney et al., Analysis and Design of Novel Electrospun PEUU Scaffolds for Soft Tissue Engineering, 2005 Annual Fall Mtg, Nov. 28-Dec. 1, 2005, Abstract L13.1, 1 page.
Courtney et al., Design and analysis of tissue engineering scaffolds that mimic soft tissue mechanical anisotropy, Biomaterials, Jul. 2006, pp. 3631-3638, vol. 27, No. 19.
Courtney et al., Incorporation of fiber tortuosity effects in a constitutive model for electrospun scaffolds, ASME 2006 Summer Bioengineering Conference, Jun. 21-25, 2006, Abstract # BI02005-157686, 2 pages.
Courtney et al., Meso- and Micromechanics of Elastomeric Electrospun PEUU Scaffolds for Cardiovascular Tissue Engineering, Regenerate World Congress on Tissue Engineering and Regenerative Medicine, Apr. 25-27, 2006, Abstract # 572, 1 page.
Courtney et al., Micromechanics of Electrospun Polyester Urethane Urea Scaffolds, Society for Biomaterials 2006 Annual Meeting, Apr. 26-29, 2006, vol. XXIX, Abstract # 163, 1 page.
Courtney et al., Micromechanics of electrospun poly ester urethane urea scaffolds for soft tissue engineering, Fifth World Congress of Biomechanics, Jul. 29-Aug. 4, 2006, Journal of Biomechanics, p. S262, vol. 39, Suppl 1.
Courtney et al., Structural and mechanical characterization of poly (ester urethane) elastomeric scaffolds for cardiovascular soft tissue engineering, Society for Biomaterials 30th Annual Meeting, Apr. 27-30, 2005, 1 page.
Dedecker et al., Small Intestinal Submucosa (SIS): prospects in urogenital surgery, Prog. Urol., Jun. 2005, vol. 15, No. 3, pp. 405-410, (English-language Abstract included).
Deglau et al., Surface Modification of Vascular Tissue for Targeted Delivery of Endothelial Cells and Microspheres, Abstract for Biomedical Engineering Society 2000 Annual Fall Meeting, Oct. 12-14, 2000, vol. 28 (Supplement), p. 23 (3 pages).
Dejardin et al., Tissue-Engineered Rotator Cuff Tendon Using Porcine Small Intestine Submucosa, Histologic and Mechanical Evaluation in Dogs, AJSM, 2001, pp. 175-184, vol. 29, No. 2.
De La Fuente et al., Evaluation of Porcine-Derived Small Intestine Submucosa as a Biodegradable Graft for Gastrointestinal Healing, Journal of Gastrointestinal Surgery, 2003, pp. 96-101, vol. 7, No. 1.
Drury et al., Hydrogels for tissue engineering: scaffold design variables and applications, Biomaterials, Nov. 2003, pp. 4337-4351, vol. 24.

(56) References Cited

OTHER PUBLICATIONS

Duruisseau et al., Endoscopic rehabilitation of vocal cord paralysis with a silicone elastomer suspension implant, Otolaryngology-Head Neck Surgery, Sep. 2004, pp. 241-247, vol. 131, No. 3.
Elbjeirami et al., Enhancing mechanical properties of tissue-engineered constructs via lysyl oxidase crosslinking activity, J Biomed Mater Res A, Sep. 2003, pp. 513-521, vol. 66, No. 3.
Feil et al., Effect of Comonomer Hydrophilicity and Ionization on the Lower Critical Solution Temperature of N-Isopropylacrylamide Copolymers, Macromolecules, 1993, pp. 2496-2500, vol. 26, No. 10.
Freytes et al., Biaxial strength of multilaminated extracellular matrix scaffolds, Biomaterials, 2004, pp. 2353-2361 vol. 25, No. 12.
Freytes et al., Porcine Urinary Bladder Matrix Derived Gel for Tissue Engineering Applications, Regenerate World Congress and Society for Biomaterials, 2006, 9 pages.
Frisk et al., A concept for miniaturized 3-D cell culture using an extracellular matrix gel, Electrophoresis, 2005, pp. 4751-4758, vol. 26.
Gelman et al., Collagen Fibril Formation Evidence for a Multistep Process, Journal of Biological Chemistry, Jan. 10, 1979, pp. 180-186, vol. 254, No. 1.
Gilbert et al., Development of a Hybrid ECM/Porous Metal Scaffold for Connective Tissue Ingrowth, Regenerate World Congress Meeting, Apr. 2006, 6 pages.
Grashow et al., Biaixal Stress-Stretch Behavior of the Mitral Valve Anterior Leaflet at Physiologic Strain Rates, Annals of Biomedical Engineering, Feb. 2006, pp. 315-325, vol. 34, No. 2.
Guan et al., Biodegradable poly(ether ester urethane)urea elastomers based on poly(ether ester) triblock copolymers and putrescine: synthesis, characterization and cytocompatibility, Biomaterials, Jan. 2004, pp. 85-96, vol. 25, No. 1.
Guan et al., Preparation and characterization of highly porous, biodegradable polyurethane scaffolds for soft tissue applications, Biomaterials, Jun. 2005, pp. 3961-3971, vol. 26, No. 18.
Guan et al., Protein-Reactive, Thermoresponsive Copolymers with High Flexibility and Biodegradability, Biomacromolecules, 2008, pp. 1283-1292, vol. 9, No. 4.
Guan et al., Synthesis, characterization, and cytocompatibility of elastomeric, biodegradable poly(ester-urethane) ureas based on poly(caprolactone) and putrescine, J Biomed Mater Res., Sep. 5, 2002, pp. 493-503, vol. 61, No. 3.
Guan et al., Synthesis, Characterization and Cytocompatibility of Polyurethaneurea Elastomers with Designed Elastase Sensitivity, Biomacromolecules, Sep.-Oct. 2005, pp. 2833-2842, vol. 6, No. 5.
Gutowska et al., Injectable Gels for Tissue Engineering, The Anatomical Record, Aug. 2001, pp. 342-349, vol. 263, No. 4.
Hacking et al., Fibrous tissue ingrowth and attachment to porous tantalum, J Biomed Mater Res, 2000, pp. 631-638, No. 52.
Han et al., Inverse thermally-reversible gelation of aqueous N-isopropylacrylamide copolymer solutions, Polymer, Jun. 1998, pp. 2809-2814, vol. 39, No. 13.
Healy et al., Designing Biomaterials to Direct Biological Responses, Annals New York Academy of Sciences, Jun. 1999, pp. 24-35, vol. 875.
Hennink et al., Novel crosslinking methods to design hydrogels, Advanced Drug Delivery Reviews, 2002, pp. 13-36, vol. 54.
Higuera et al., Tendon reattachment to a metallic implant using an allogenic bone plate augmented with rhOP-1 vs. autogenous cancellous bone and marrow in a canine model, Journal of Orthopaedic Research, Sep. 2005, pp. 1091-1099, vol. 23, No. 5.
Williams et al., Collagen Fibril Formation Optimal In Vitro Conditions and Preliminary Kinetic Results, The Journal of Biological Chemistry, Sep. 25, 1978, pp. 6578-6585, vol. 253, No. 18.
Wood et al., Use of a particulate extracellular matrix bioscaffold for treatment of acquired urinary incontinence in dogs. JAVMA, Apr. 1, 2005, pp. 1095-1097, vol. 226, No. 7.
Wright Medical Technology, Comparative Analysis: Graft Jacket™ Periosteum Replacement Scaffold & SIS™ Porcine Small Intestine Submucosa, Copyright in 2002, 6 pages.
Xu et al., Aligned biodegradable nanofibrous structure: a potential scaffold for blood vessel engineering, Biomaterials, Feb. 2004, pp. 877-886, vol. 25, No. 5.
Xu et al., Injectable Tissue-Engineered Cartilage with Different Chondrocyte Sources, Plastic and Reconstructive Surgery, Apr. 15, 2004, pp. 1361-1371, vol. 113, No. 5.
Zantop et al., Extracellular Matrix Scaffolds are Repopulated by Bone Marrow-Derived Cells in a Mouse Model of Achilles Tendon Reconstruction, Journal of Orthopaedic Research, Jun. 2006, pp. 1299-1309, vol. 24, No. 6.
Zhang et al., Artificial Matrix Helps Neonatal Cardiomyocytes Restore Injured Myocardium in Rats, Artificial Organs, Feb. 2006, pp. 86-93, vol. 30, No. 2.
Hoerstrup et al., Tissue engineering of small caliber vascular grafts, European Journal of Cardio-Thoracic Surgery, Jul. 2001, pp. 164-169, vol. 20.
Ibusuki et al., Tissue-Engineered Cartilage Using an Injectable and in Situ Gelable Thermoresponsive Gelatin: Fabrication and in Vitro Performance, Tissue Engineering, 2003, pp. 371-384, vol. 9, No. 2.
Karlon et al., Automated Measurement of Myofiber Disarray in Transgenic Mice With Ventricular Expression of ras, The Anatomical Record, Dec. 1998, pp. 612-625, vol. 252, No. 4.
Kim et al., Synthesis and Characterization of Injectable Poly(N-isopropylacrylamide-co-acrylic acid) Hydrogels with Proteolytically Degradable Cross-Links, Biomacromolecules, Sep.-Oct. 2003, pp. 1214-1223, vol. 4, No. 5.
Kim et al., Synthetic MMP-13 degradable ECMs based on poly(N-isopropylacrylamide-co-acrylic acid) semi-interpreting polymer networks. I. Degradation and cell migration, J Biomed Mater Res A, Oct. 2005, pp. 73-88, vol. 75, No. 1.
Lee et al., Copolymers of N-isopropylacrylamide, HEMA-lactate and acrylic acid with time-dependent lower critical solution temperature as a bioresorbable carrier, Polym Int, Feb. 2005, pp. 418-422, vol. 54, No. 2.
Lee et al., In situ-Gelling, Erodible N-Isopropylacrylamide Copolymers, Macromol Biosci., Jul. 14, 2005, pp. 629-635, vol. 5, No. 7.
Lee et al., Nanofiber alignment and direction of mechanical strain affect the ECM production of human ACL fibroblast, Biomaterials, Apr. 2005, pp. 1261-1270, vol. 26, No. 11.
Lehman et al., Injectable and Bulk-Forming Agents for Enhancing the Lower Esophageal Sphincter, Am J Med. Aug. 18, 2003, pp. 188S-191S, vol. 115, Suppl. 3A.
Li et al., Cellular and nerve regeneration within a biosynthetic extracellular matrix for corneal transplantation, Proc Natl Acad Sci USA, Dec. 23, 2003, pp. 15346-15351, vol. 100, No. 26.
Li et al., Recruitment of multiple cell lines by collagen-synthetic copolymer matrices in corneal regeneration, Biomaterials, Jun. 2005, pp. 3093-3104, vol. 26, No. 16.
Lightner et al., Injectable Agents: Present and Future, Curr Urol Rep., Oct. 2002, pp. 408-413, vol. 3, No. 5.
Makino et al., Kinetics of swelling and shrinking poly(N-isopropylacrylamide) hydrogels at different temperatures, Colloids and Surfaces B: Biointerfaces, Dec. 2000, pp. 197-204, vol. 19, No. 2.
Matsuda et al., Mechano-active scaffold design of small-diameter artificial graft made of electrospun segmented polyurethane fabrics, J Biomed Mater Res A, Apr. 1, 2005, pp. 125-131, vol. 73, No. 1.
Matsumaru et al., Application of thermosensitive polymers as a new embolic material for intravascular neurosurgery, J Biomater Sci Polymer Edn, 1996, pp. 795-804, vol. 7, No. 9.
Middleton et al., Synthetic Biodegradable Polymers as Medical Devices, Medical Plastics and Biomaterials Magazine, Mar. 1998, 10 pages.
Nancollas, In vitro Studies of Calcium Phosphate Crystallization, Biomineralization: Chemical and Biochemical Perspectives, 1989, pp. 157-187, VCH, New York.
Nedovic et al., Cell immobilisation by electrostatic droplet generation, Landbauforschung Volkenrode, 2002, pp. 11-17, No. 241.
Nelson et al., Intra-myocardial biomaterial injection therapy in the treatment of heart failure: Materials, outcomes and challenges, Acta Biomaterialia, 2011, pp. 1-15, vol. 7.

(56) References Cited

OTHER PUBLICATIONS

Neradovic et al, Poly(N-isopropylacrylamide) with hydrolyzable lactic acid ester side groups: a new type of thermosensitive polymer, Macromol. Rapid Commun., Oct. 1999, pp. 577-581, vol. 20, No. 11.

Ohya et al., Poly(N-isopropylacrylamide) (PNIPAM)-grafted gelatin as thermoresponsive three-dimensional artificial extracellular matrix: molecular and formulation parameters vs. cell proliferation potential, J Biomater Sci Polymer Edn, 2005, pp. 809-827, vol. 16, No. 7.

Ohya et al., Thermoresponsive Artificial Extracellular Matrix for Tissue Engineering: Hyaluronic Acid Bioconjugated with Poly(N-isopropylacrylamide) Grafts, Biomacromolecules, Fall 2001, pp. 856-863, vol. 2, No. 3.

Opitz et al., Tissue Engineering of Ovine Aortic Blood Vessel Substitutes Using Applied Shear Stress and Enzymatically Derived Vascular Smooth Muscle Cells, Annals of Biomedical Engineering, Feb. 2004, pp. 212-222, vol. 32, No. 2.

Radisic et al., Medium perfusion enables engineering of compact and contractile cardiac tissue. Am J Physiol Heart Circ Physiol, Feb. 2004, pp. H507-H516, vol. 286, No. 2.

Ray et al., Isolation of vascular smooth muscle cells from a single murine aorta, Methods in Cell Science, 2002, pp. 185-188, vol. 23, No. 4.

Reddy et al., A Simplified Method for the Analysis of Hydroxyproline in Biological Tissues, Clinical Biochemistry, Jun. 1996, pp. 225-229, vol. 29, No. 3.

Riboldi et al., Electrospun degradable polyesterurethane membranes: potential scaffolds for skeletal muscle tissue engineering, Biomaterials, Aug. 2005, pp. 4606-4615, vol. 26, No. 22.

Rimsay et al., Biochemical analysis of hyaline gelation: an essential step in the assembly of the sea urchin extraembryonic matrix, the hyaline layer, Archives of Biochemistry and Biophysics, 2003, pp. 279-286, vol. 414.

Ringel et al., The Application of Tissue Engineering Procedures to Repair the Larynx, Journal of Speech, Language and Hearing Research, Feb. 2006, pp. 194-208, vol. 49, No. 1.

Robinson et al., Extracellular Matrix Scaffold for Cardiac Repair, Circulation, Aug. 30, 2005, pp. I-135-I-143, vol. 112.

Robinson, Roles for Ca2+, Mg2+ and NaCl in modulating the self-association reaction of hyalin, a major protein component of the sea-urchin extraembryonic hyaline layer, Biochem J., Nov. 15, 1988, pp. 225-228, vol. 256, No. 1.

Sacks, Biaxial Mechanical Evaluation of Planar Biological Materials, Journal of Elasticity, 2000, pp. 199-246, vol. 61, Nos. 1-3.

Santucci et al., Resorbable extracellular matrix grafts in urologic reconstruction, International Braz J Urol., May-Jun. 2005, pp. 192-203, vol. 31, No. 3.

Sarikaya et al., Antimicrobial Activity Associated with Extracellular Matrices, Tissue Engineering, Feb. 2002, pp. 63-71, vol. 8, No. 1.

Schmedlen et al., Photocrosslinkable polyvinyl alcohol hydrogels that can be modified with cell adhesion peptides for use in tissue engineering, Biomaterials, Nov. 2002, pp. 4325-4332, vol. 23, No. 22.

Schmolka, Artificial Skin I. Preparation and Properties of Pluronic F-127 Gels for Treatment of Burns, J Biomed Mater Res, 1972, pp. 571-582, vol. 6, No. 6.

Shimizu et al., Fabrication of Pulsatile Cardiac Tissue Grafts Using a Novel 3-Dimensional Cell Sheet Manipulation Technique and Temperature-Responsive Cell Culture Surfaces, Circulation Research, Feb. 22, 2002, pp. e40-e48, vol. 90, No. 3.

Stankus et al., Fabrication of biodegradable elastomeric scaffolds with sub-micron morphologies, J Biomed Mater Res A, Sep. 15, 2004, pp. 603-614, vol. 70, No. 4.

Stankus et al. Fabrication of cell microintegrated blood vessel constructs through electrohydrodynamic atomization, Biomaterials, Jun. 2007, pp. 2738-2746, vol. 28, No. 17.

Stankus et al., Microintegrating smooth muscle cells into a biodegradable, elastomeric fiber matrix, Biomaterials, Feb. 2006, pp. 735-744, vol. 27, No. 5.

Stile et al., Thermo-Responsive Peptide-Modified Hydrogels for Tissue Regeneration, Biomacromolecules, Spring 2001, pp. 185-194, vol. 2.

Suwiwat et al., Expression of Extracellular Matrix Components Versican, Chondroitin Sulfate, Tenascin, and Hyaluronan, and Their Association with Disease Outcome in Node-Negative Breast Cancer, Clinical Cancer Research, Apr. 1, 2004, pp. 2491-2498, vol. 10.

Temple et al., Electrostatic transportation of living cells through air, Abstracts of Papers, 223 ACS National Meeting, Apr. 7-11, 2002, 1 page.

Tiwari et al., Development of a hybrid cardiovascular graft using a tissue engineering approach, The FASEB Journal, Jun. 2002, pp. 791-796, vol. 16, No. 8.

Tous et al., Influence of Injectable Hyaluronic Acid Hydrogel Degradation Behavior on Infarction-Induced Ventricular Remodeling, Biomacromolecules, 2011, pp. 4127-4135, vol. 12.

Van Dijk-Wolthuis et al., A new class of polymerizable dextrans with hydrolyzable groups: hydroxyethyl methacrylated dextran with and without oligolactate spacer, Polymer, Dec. 1997, pp. 6235-6242, vol. 38, No. 25.

Veazey et al., Mammalian Cell Delivery via Aerosol Deposition, J Biomed Mater Res B Appl Biomater, Feb. 15, 2005, pp. 334-338, vol. 72, No. 2.

Venere, New materials hold promise for human healing applications, Purdue News, Mar. 22, 2001, 4 pages.

Vihola et al., Cytotoxicity of thermosensitive polymers poly(N-isopropylacrylamide), poly(N-vinylcaprolactam) and amphiphilically modified poly(N-vinylcaprolactam), Biomaterials, Jun. 2005, pp. 3055-3064, vol. 26, No. 16.

Wall et al., Theoretical Impact of the Injection of Material Into the Myocardium: A Finite Element Model Simulation, Circulation, Dec. 12, 2006, pp. 2627-2635, vol. 114.

\* cited by examiner

Week 2

Week 4

Week 2

Week 4

Week 2            Week 4

Week 2          Week 4

Week 2

Week 2

Week 4

BIOHYBRID COMPOSITE SCAFFOLD

STATEMENT REGARDING FEDERAL FUNDING

This invention was made with government support under Grant No. W81XWH-08-2-0032 awarded by the Army/MRMC. The government has certain rights in the invention.

Biologic scaffolds composed of extracellular matrix (ECM) are utilized in numerous regenerative medicine applications to facilitate the constructive remodeling of tissues and organs. The mechanisms by which the host remodeling response occurs are not fully understood, but recent studies suggest that both constituent growth factors and biologically active degradation products derived from ECM play important roles.

The extracellular matrix (ECM) represents the secreted product of resident cells within every tissue and organ and thus defines a preferred collection of structural and functional molecules best suited to support the viability and phenotype of those cells. The ECM is in a state of dynamic reciprocity with the cells of each tissue, and the growth factors, cytokines, chemokines, and other signaling molecules within the ECM play important roles in development, homeostasis, and response to injury. A variety of mammalian tissues and organs, including the small intestine, liver, urinary bladder, arterial vasculature, heart valves, and dermis, have been decellularized, and the remaining ECM used as a biologic scaffold to support the reconstruction of injured or missing tissues. The mechanisms by which these biologic scaffolds facilitate tissue remodeling include both contact guidance and molecular signaling, but the temporal and spatial patterns of these events remain largely unknown.

SUMMARY

A novel biohybrid scaffold is generated here by concurrent extracellular matrix (ECM) gel electrospraying and biodegradable elastomer electrospinning. ECM gel possesses good bioactivity and biocompatibility, but its weak mechanic properties and fast degradation limits its clinical applications. Biodegradable elastomer can be processed into the sub-micro fibrous scaffold using electrospinning. This electrospun scaffold has attractive mechanical behaviors and good cytocompatibility, however, it exhibits poor cellular penetration and tissue integration due to its dense structure, which would delay the tissue formation and healing. A biohybrid elastic scaffold is therefore provided which is fabricated by concurrent electrospray/electrospinning, and comprises interpenetrated ECM gel and elastomer fibers, where ECM gel would make the electrospun scaffold looser and provide the bioactivity and biocompatibility to accelerate cellular and tissue integration and growth, while the elastomeric polymer fibers improve the mechanical properties of the scaffold structure. The elastic biohybrid scaffold is useful for clinical applications in tissue repair and replacement.

According to one embodiment, a concurrent gel electrospray/polymer electrospinning method is provided to obtain a biohybrid composite of extracellular matrix (ECM) gel/biodegradable elastomeric fibers. The method comprises electrospinning a biodegradable, biocompatible, elastomeric polymer composition onto a substrate and concurrently or substantially concurrently electrospraying an ECM-derived (extracellular matrix-derived) gel onto the substrate. In one embodiment, the substrate is a mandrel, which is rotated during electrospinning. Non-limiting examples of biodegradable, biocompatible, elastomeric polymer composition include: PEUU-, PEEUU-, PCUU-, PECUU-, PET- (e.g., DACRON), and TPA-containing compositions.

According to another non-limiting embodiment, one or more layers of a wet-electrospun biodegradable, biocompatible, elastomeric polymer composition are electrospun onto the layer of biodegradable, biocompatible, elastomeric polymer composition mixed with the ECM gel. In one embodiment, the layer of biodegradable, biocompatible, elastomeric polymer composition mixed with the ECM gel is sandwiched between two electrospun layers of the wet-electrospun biodegradable, biocompatible, elastomeric polymer composition.

In one embodiment, the biodegradable, biocompatible elastomeric polymer comprises one of PEUU, PEEUU or a mixture thereof. In another embodiment, the biodegradable, biocompatible elastomeric polymer comprises polycaprolactone, which has an Mw (weight average molecular weight) of 1000-5000, and in one embodiment, the polycaprolactone has an Mw of 2000. As an example, the biodegradable, biocompatible elastomeric polymer comprises, consists essentially of or consists of a copolymer of polycaprolactone (Mw~2000), 1,4-diisocyanobutane and putrescine. In yet another embodiment, the biodegradable, biocompatible elastomeric polymer is prepared from a polycaprolactone-polyethylene glycolpolycaprolactone triblock copolymer, an aliphatic diisocyanate and an aliphatic diamine, for example, the aliphatic diisocyanate is 1,4-diisocyanobutane and the aliphatic diamine is putrescine. In certain embodiments, the ECM-derived gel is prepared from dermal ECM, urinary bladder ECM and/or small intestine ECM.

In the composition and related methods, the scaffold (scaffold structure) comprises >50% wt of the biodegradable, biocompatible elastomeric polymer, for example and without limitation, the scaffold comprises from 70% to 85% wt of the biodegradable, biocompatible elastomeric polymer, for example approximately 72% wt.

In an alternate embodiment, a multi-layered structure is produced comprising the above-described ECM gel/polymer electrospun composition attached to or sandwiched between one or more wet-electrospun layers of a biodegradable, biocompatible, elastomeric polymer. The method comprises concurrently or substantially concurrently electrospinning a biodegradable, biocompatible, elastomeric polymer and spraying a liquid, such as an aqueous liquid, for example and without limitation a liquid selected from the group consisting of water, a physiological salt solution (e.g., normal saline), a buffer solution (e.g., PBS), a mammalian blood product and cell culture medium, onto the substrate, thereby producing a first layer, and concurrently or substantially concurrently electrospinning the biodegradable, biocompatible, elastomeric polymer matrix and electrospraying the ECM-derived (extracellular matrix-derived) gel onto the matrix onto the first layer, thereby producing a second layer. In certain embodiments, the method comprises concurrently or substantially concurrently electrospinning a biodegradable, biocompatible, elastomeric polymer and spraying a liquid, such as an aqueous liquid, for example and without limitation a liquid selected from the group consisting of water, a physiological salt solution (e.g., normal saline), a buffer solution (e.g., PBS), a mammalian blood product and cell culture medium, onto the second layer, thereby producing a third layer. As an example, the biodegradable, biocompatible, elastomeric polymer composition comprises one or more of: PEUU-, PEEUU-, PCUU-, PECUU-, PET- (e.g., DACRON), and TPA-containing compositions, for example, one or both of a poly(ester urethane)urea (PEUU) and a poly(ether ester urethane)urea (PEEUU).

Alternately, the method comprises after electrospinning the biodegradable, biocompatible, elastomeric polymer composition onto the substrate and concurrently or substantially concurrently electrospraying an ECM-derived (extracellular matrix-derived) gel onto the substrate, concurrently or substantially concurrently electrospinning a biodegradable, biocompatible, elastomeric polymer and spraying a liquid, such as an aqueous liquid, for example and without limitation a liquid selected from the group consisting of water, a physiological salt solution, a buffer solution, a mammalian blood product and cell culture medium, onto the substrate.

Also provided is biohybrid scaffold (e.g., scaffold structure, structure or device) comprising a matrix of a biodegradable, biocompatible elastomeric polymer and an ECM-derived gel interspersed substantially evenly throughout the matrix. As indicated above, examples of the biodegradable, biocompatible elastomeric polymer include one or more of: PEUU-, PEEUU-, PCUU-, PECUU-, PET- (e.g., DACRON), and TPA-containing compositions. In one non-limiting embodiment, the biodegradable, biocompatible elastomeric polymer comprises a copolymer of polycaprolactone (Mw~2000), 1,4-diisocyanobutane and putrescine. In additional embodiments, the biohybrid scaffold further comprises one or more layers of a wet-electrospun biodegradable, biocompatible elastomeric polymer attached to the matrix of a biodegradable, biocompatible elastomeric polymer and the ECM-derived gel interspersed substantially evenly throughout the matrix, forming a composite scaffold structure. In another embodiment, the composite scaffold comprises the matrix of a biodegradable, biocompatible elastomeric polymer and an ECM-derived gel interspersed substantially evenly throughout the matrix sandwiched between two layers of the wet-electrospun biodegradable, biocompatible elastomeric polymer. According to one embodiment, the wet-electrospun biodegradable, biocompatible elastomeric polymer comprises a PEUU and PBS, or one or more of an aqueous liquid, for example and without limitation a liquid selected from the group consisting of water, a physiological salt solution, a buffer solution, a mammalian blood product and cell culture medium.

Uses for the scaffold structures described herein include a method of growing tissue in a patient comprising implanting a biohybrid scaffold according to any embodiment described herein in a patient at a site of injury or defect in the patient. As an example, the biohybrid scaffold is implanted in an abdominal wall the patient, thereby repairing an injury or defect in the abdominal wall of the patient.

BRIEF DESCRIPTION OF THE DRAWINGS

In FIGS. 9A and 9B, the right and left images are from different areas of the implant in a single rat.

In FIGS. 10A and 10B, the right and left images are from different areas of the implant in a single rat.

DETAILED DESCRIPTION

Figure 1:
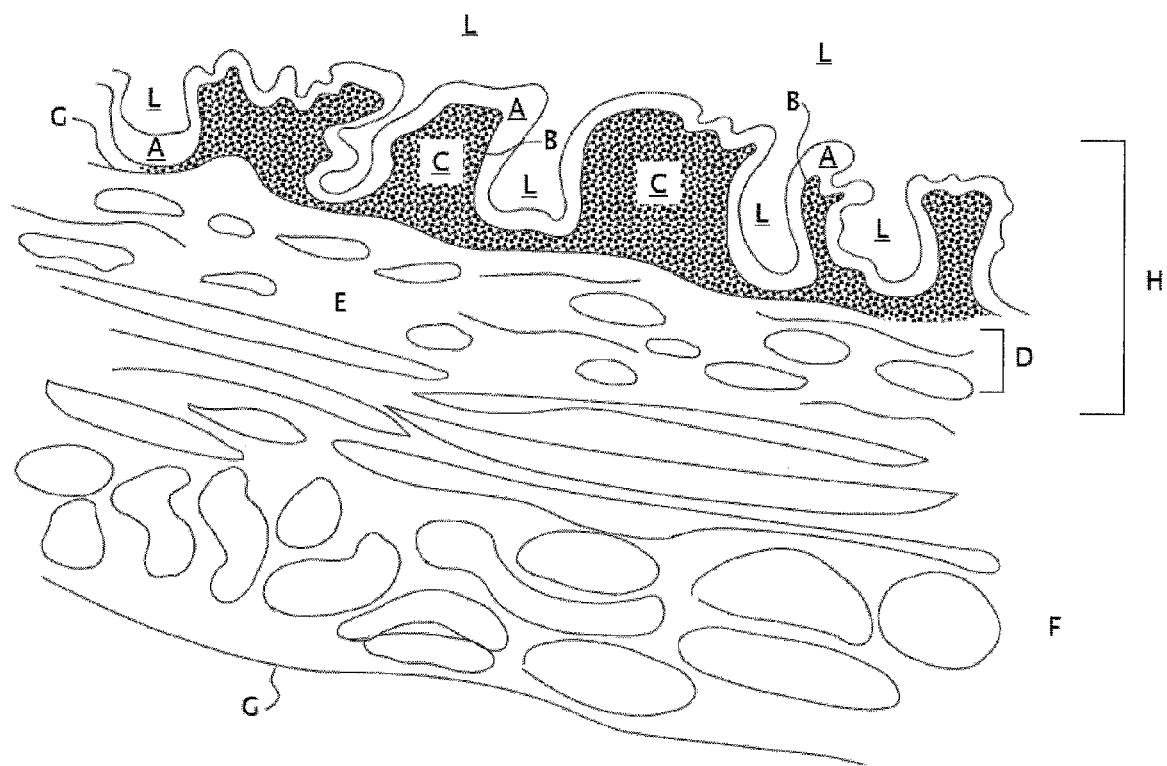
FIG. 1 is a schematic diagram of a cross section or porcine urinary bladder tissue.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values.

As used herein, the "treatment" or "treating" of a wound or defect means administration to a patient by any suitable dosage regimen, procedure and/or administration route of a composition, device or structure with the object of achieving a desirable clinical/medical end-point, including attracting progenitor cells, healing a wound, correcting a defect, etc.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings and "mammal" refers to all mammals, including, but not limited to human beings.

A biodegradable polymer composition is "biocompatible" in that the polymer and degradation products thereof are substantially non-toxic to cells or organisms within acceptable tolerances, including substantially non-carcinogenic and substantially non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas copolymers contain more than one type of monomer. The term "(co)polymer" and like terms refer to either homopolymers or copolymers.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain groups are missing and/or modified when incorporated into the polymer backbone. A polymer is said to comprise a specific type of linkage if that linkage is present in the polymer.

As described herein, a "fiber" an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning) and can be isotropic or anisotropic.

By "biodegradable or "bioerodable", it is meant that a polymer, once implanted and placed in contact with bodily fluids and tissues, will degrade either partially or completely through chemical reactions with the bodily fluids and/or tissues, typically and often preferably over a time period of hours, days, weeks or months. Non-limiting examples of such chemical reactions include acid/base reactions, hydrolysis reactions, and enzymatic cleavage. The biodegradation rate of the polymer matrix may be manipulated, optimized or otherwise adjusted so that the matrix degrades over a useful time period. The polymer or polymers typically will be selected so that it degrades in situ over a time period to optimize mechanical conditioning of the tissue. For instance, in the case of abdominal wall repair, it is desirable that the matrix dissolves over at least a week and preferably longer. More importantly, the matrix would have to retain its supportive capacity until tissue remodeling occurs, such as for at least 2-8 weeks, or longer.

According to a first embodiment, the structures described herein comprise a biodegradable, elastomeric polymer component and an ECM gel component. As used herein, compositions of matter comprising the described polymeric components and ECM gel, optionally in combination with additional layers, such as wet-electrospun layers, are generically referred to herein as "scaffolds" and "structures," which includes as a class, without limitation, scaffolds, matrices, biological scaffolds or matrices, cell growth scaffolds or matrices, etc. The typical biodegradable, elastomeric polymer component, when implanted, shows limited cellular infiltration. The ECM gel component, while useful in promoting cell growth (including, but not limited to one or more of colonization, propagation, infiltration, cell viability, differentiation, tissue repair), has insubstantial strength for use as a tissue repair scaffold in a patient that requires physical strength. It has been found that a simple 50-50 (50% biodegradable, elastomeric polymer:50% ECM gel (1:1), by dry weight of the polymer) mixture of biodegradable, elastomeric polymer to ECM gel is not optimal. Applicants have determined that the ratio of biodegradable, elastomeric polymer to ECM gel that shows excellent cellular infiltration, while displaying adequate tensile strength and elasticity, is >50%: <50% and preferably from 70%-85%:15%-30%. This can be achieved by codepositing the biodegradable, elastomeric polymer and the ECM gel by e.g., electrospinning. As described herein, the biodegradable, elastomeric polymer is electrospun and the ECM gel is sprayed, e.g. electrosprayed.

The ECM gels described herein are derived from ECM-derived scaffold material. An "ECM-derived material," is a material prepared from an extracellular matrix-containing tissue. Any type of extracellular matrix scaffold material can be used to produce the gels in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). In certain embodiments, the ECM is isolated from a vertebrate animal, for example and without limitation, from a mammal, including, but not limited to, human, monkey, pig, cow and sheep. The ECM can be derived from any organ or tissue, including without limitation, urinary bladder, intestine, liver, esophagus and dermis. In one embodiment, the ECM is isolated from a urinary bladder. The ECM may or may not include the basement membrane portion of the ECM. In certain embodiments, the ECM includes at least a portion of the basement membrane.

In one embodiment, the ECM is isolated from harvested porcine urinary bladder to prepare urinary bladder matrix (UBM). Excess connective tissue and residual urine are removed from the urinary bladder. The tunica serosa, tunica muscularis externa, tunica submucosa and most of the muscularis mucosa (layers G, F, E and mostly D in FIG. 1) can be removed mechanical abrasion or by a combination of enzymatic treatment, hydration, and abrasion. Mechanical removal of these tissues can be accomplished by abrasion using a longitudinal wiping motion to remove the outer layers (particularly the abluminal smooth muscle layers) and even the luminal portions of the tunica mucosa (epithelial layers). Mechanical removal of these tissues is accomplished by removal of mesenteric tissues with, for example, Adson-Brown forceps and Metzenbaum scissors and wiping away the tunica muscularis and tunica submucosa using a longitudinal wiping motion with a scalpel handle or other rigid object wrapped in moistened gauze. The epithelial cells of the tunica mucosa (layer A of FIG. 1) can also be dissociated by soaking the tissue in a de-epithelializing solution, for example and without limitation, hypertonic saline. The resulting UBM comprises basement membrane of the tunica mucosa and the adjacent tunica propria (layers B and C of FIG. 1), which is further treated with peracetic acid, lyophilized and powdered. Additional examples are provided below and are also present in the related art.

In another embodiment, the epithelial cells can be delaminated first by first soaking the tissue in a de-epithelializing solution such as hypertonic saline, for example and without limitation, 1.0 N saline, for periods of time ranging from 10 minutes to 4 hours. Exposure to hypertonic saline solution effectively removes the epithelial cells from the underlying basement membrane. The tissue remaining after the initial delamination procedure includes epithelial basement membrane and the tissue layers abluminal to the epithelial basement membrane. This tissue is next subjected to further treatment to remove the majority of abluminal tissues but not the epithelial basement membrane. The outer serosal, adventitial, smooth muscle tissues, tunica submucosa and most of the muscularis mucosa are removed from the remaining de-epithelialized tissue by mechanical abrasion or by a combination of enzymatic treatment, hydration, and abrasion.

In one embodiment, the ECM is prepared by abrading porcine bladder tissue to remove the outer layers including both the tunica serosa and the tunica muscularis (layers G and F in FIG. 1) using a longitudinal wiping motion with a scalpel handle and moistened gauze. Following eversion of the tissue segment, the luminal portion of the tunica mucosa (layer H in FIG. 1) is delaminated from the underlying tissue using the same wiping motion. Care is taken to prevent perforation of the submucosa (layer E of FIG. 1). After these tissues are removed, the resulting ECM consists mainly of the tunica submucosa (layer E of FIG. 1).

ECM-derived material can be decelluarized, sterilized and/or dried by any useful method. ECM-derived material can then be used in any form in the methods and compositions described herein. For instance, the compounds described herein can be applied to sheets of ECM or comminuted ECM to prepare a scaffold suitable to apply to any location in a patient, such as a skin, cartilage, muscle, bone, or nerve growth scaffold.

The ECM can be sterilized by any of a number of standard methods without loss of its ability to induce endogenous tissue growth. For example, the material can be sterilized by propylene oxide or ethylene oxide treatment, gamma irradiation treatment (0.05 to 4 mRad), gas plasma sterilization, peracetic acid sterilization, or electron beam treatment. The material can also be sterilized by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. More typically, ECM is disinfected by immersion in 0.1% (v/v) peracetic acid (a), 4% (v/v) ethanol, and 96% (v/v) sterile water for 2 h. The ECM material is then washed twice for 15 min with PBS (pH=7.4) and twice for 15 min with deionized water.

Commercially available ECM preparations can also be used in the methods, devices and compositions described herein. In one embodiment, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another embodiment, the ECM is derived from dermis. Commercially available preparations include, but are not limited to Pelvicol™ (crosslinked porcine dermal collagen, sold as Permacol™ in Europe; Bard Medical Division, Covington, Ga.), Repliform™ (Microvasive; Boston, Mass.) and Alloderm™ (LifeCell; Branchburg, N.J.). In another embodiment, the ECM is derived from urinary bladder. Commercially available preparations include, but are not limited to UBM (Acell Corporation; Jessup, Md.).

An extracellular matrix-derived gel is described herein. In its broadest sense, ECM-derived scaffold materials are comminuted and solubilized to form a hydrogel. The solubilized hydrogel may or may not be dialyzed. Solubilization may be achieved by digestion with a suitable protease, such as the endoproteases trypsin, chymotrypsin, pepsin, papain and elastase. In certain non-limiting embodiments, the method for making such a gel comprises: (i) comminuting an extracellular matrix, (ii) solubilizing intact, non-dialyzed or non-crosslinked extracellular matrix by digestion with an acid protease in an acidic solution to produce a digest solution, (iii) raising the pH of the digest solution to a pH between 7.2 and 7.8 to produce a neutralized digest solution, and (iv) gelling the solution at a temperature greater than approximately 25° C.

As described above, the ECM typically is derived from mammalian tissue, such as, without limitation from one of urinary bladder, dermis, spleen, liver, heart, pancreas, ovary, or small intestine. In one embodiment, the ECM-derived scaffold material is crosslinked porcine dermal collagen, e.g., Pelvicol™ (Bard Medical Division, Covington, Ga.) In certain embodiments, the ECM is derived from a pig, cow, horse, monkey, or human. In one non-limiting embodiment, the ECM is lyophilized and comminuted. The ECM is then solubilized with an acid protease. The acid protease may be, without limitation, pepsin or trypsin, and in one embodiment is pepsin. The ECM typically is solubilized at an acid pH suitable or optimal for the protease, such as greater than about pH 2, or between pH 2 and 4, for example in a 0.01M HCl solution. The solution typically is solubilized for 12-48 hours, depending upon the tissue type (e.g., see examples below), with mixing (stirring, agitation, admixing, blending, rotating, tilting, etc.). Once the ECM is solubilized the pH is raised to between 7.2 and 7.8, and according to one embodiment, to pH 7.4. Bases, such as bases containing hydroxyl ions, including NaOH, can be used to raise the pH of the solution. Likewise buffers, such as an isotonic buffer, including, without limitation, Phosphate Buffered Saline (PBS), can be used to bring the solution to a target pH, or to aid in maintaining the pH and ionic strength of the gel to target levels, such as physiological pH and ionic conditions. The neutralized digest solution can be gelled at temperatures approaching 37° C., typically at any temperature over 25° C., though gelation proceeds much more rapidly at temperatures over 30° C., and as the temperature approaches physiological temperature. The method typically does not include a dialysis step prior to gelation, yielding a more-complete ECM-like matrix that typically gels at 37° C. more slowly than comparable collagen or dialyzed ECM preparations.

The ECM gel can be sprayed as a liquid or hydrogel in the methods provided herein. An ECM gel may have an LCST (Lower Critical Solution Temperature) above or below the temperature at which the solution is sprayed, and as such will have a gel transition at a temperature higher, equal to or lower than the temperature at which the ECM gel is sprayed. For example, if the hydrogel is sprayed at room temperature (that is approximately 20-25° C.) or less and the LCST of the ECM material is greater than the spraying temperature, but, e.g., less than 37° C., the material can be sprayed and will later gel on warming, for example on implantation. Thus, an ECM gel with an LCST between 20° C. and 37° C., for example and without limitation approximately 25° C., is useful in the compositions and methods described herein. See, e.g. United States Patent Publication No. 20080260831, incorporated herein by reference for its technical disclosure. See also, Stankus et al., Hybrid nanofibrous scaffolds from electrospinning of a synthetic biodegradable elastomer and urinary bladder matrix, J Biomater. Sci. Polym. Ed. (2008) 19(5):635-652. In that reference, PEUU was mixed with solubilized UBM ECM and was electrospun. Although UBM prepared in this manner may find use co-electrospun with PEUU rather than electrospun in the same mixture, cells do not permeate the matrix of that reference as well as desired or as well as the scaffolds described herein. The ECM gel, when electrosprayed, is not necessarily a gel at that time, but is indicated as being a gel due to its final, intended physical form in the scaffold structures described herein, and thus the phrase "ECM gel" includes pre-gels—compositions that are in the process of gelling when electrosprayed, or which are gelled in the scaffold product, e.g., by heating to 37° C.

As used herein, the term "polymer" refers to both synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions, described above. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, as a non-woven mesh formed by electrospinning.

Generally, the polymeric components suitable for the structures described herein are any polymer that is biocompatible and can be biodegradable. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters, anhydrides, polyanhydrides, or amides, which can be useful in, for example and without limitation, controlling the degradation rate of the scaffold and/or the release rate of therapeutic agents from the scaffold. Alternatively, the polymer(s) may contain polypeptides or biomacromolecules as building blocks which are susceptible to chemical reactions once placed in situ. In one non-limiting example, the polymer composition comprises a polypeptide comprising the amino acid sequence alanine-alanine-lysine, which confers enzymatic lability to the polymer. In another non-limiting embodiment, the polymer composition may comprise a biomacromolecular component derived from an ECM. For example, as described in further detail below, the polymer composition may comprise the biomacromolecule collagen so that collagenase, which is present in situ, can degrade the collagen. The polymers used herein may be elastomeric, meaning they change shape on application of a deforming force and substantially return to an original shape when the deforming force is removed.

In another non-limiting embodiment, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

A number of biocompatible, biodegradable elastomeric (co)polymers are known and have been established as useful in preparing cell growth matrices, including biodegradable poly(ester urethane) urea (PEUU), poly(ether ester urethane) urea (PEEUU), poly(ester carbonate)urethane urea (PECUU) and poly(carbonate)urethane urea (PCUU). In general, useful (co)polymers comprise monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polygalactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

In certain embodiments, the polymers used to make the structures described herein also release therapeutic agents when they degrade within the patient's body. For example, the individual building blocks of the polymers may be chosen such that the building blocks themselves provide a therapeutic benefit when released in situ through the degradation process. In one embodiment, one of the polymer building blocks is putrescine, which has been implicated as a substance that causes cell growth and cell differentiation.

The biodegradable polymers may be, without limitation, homopolymers, copolymers, and/or polymeric blends. According to certain embodiments, the polymer(s) comprise, without limitation, one or more of the following monomers: glycolide, lactide, caprolactone, dioxanone, and trimethylene carbonate. According to certain embodiments, the polymer is chosen from one or more of: a polymer derived from an alpha-hydroxy acid, a polylactide, a poly(lactide-co-glycolide), a poly(L-lactide-co-caprolactone), a polyglycolic acid, a poly(dl-lactide-co-glycolide), a poly(1-lactide-co-dl-lactide), a polymer comprising a lactone monomer, a polycaprolactone, polymer comprising carbonate linkages, a polycarbonate, a polyglyconate, a poly(trimethylene carbonate), a poly(glycolide-co-trimethylene carbonate), a poly(glycolide-co-trimethylene carbonate-co-dioxanone), a polymer comprising urethane linkages, a polyurethane, a poly(ester urethane) urea, a poly(ester urethane) urea elastomer, a poly(ester carbonate urethane) urea, a poly(carbonate urethane) urea, a polycarbonate urethane, a polyester urethane, a polymer comprising ester linkages, a polyalkanoate, a polyhydroxybutyrate, a polyhydroxyvalerate, a polydioxanone, a polygalactin, a natural polymer, chitosan, collagen, elastin, alginate, cellulose, hyaluronic acid and gelatin. In one embodiment, the polymer composition comprises a poly(ester urethane) urea with from about 25% wt. to about 75% wt. collagen. The polymer composition also may comprise elastin, collagen or a mixture thereof, for example and without limitation from about 25% wt. to about 75% wt. of a mixture of collagen and elastin, which are, according to one embodiment, in approximately (about) equal amounts. In one non-limiting embodiment, the polymer comprises a polycaprolactone. In another embodiment, the polymer comprises a polycaprolactone diol. In yet another embodiment, the polymer comprises a triblock copolymer comprising polycaprolactone, poly(ethylene glycol), and polycaprolactone blocks In another non-limiting embodiment, the polymer composition may comprise a biomacromolecular component derived from an ECM. For example, the polymer composition may comprise the biomacromolecule collagen so that collagenase, which is present in situ, can degrade the collagen. According to a non-limiting embodiment, the polymer composition comprises one or both of a collagen and an elastin. Collagen is a common ECM component and typically is degraded in vivo at a rate faster than many synthetic bioerodable polymers. Therefore, manipulation of collagen content in the polymer composition can be used as a method of modifying bioerosion rates in vivo. Collagen may be present in the polymer composition in any useful range, including, without limitation, from about 2% wt. to about 95% wt., but more typically in the range of from about 25% wt. to about 75% wt., inclusive of all ranges and points therebetween, including from about 40% wt. to about 75% wt., including about 75% wt. and about 42.3% wt. Elastin may be incorporated into the polymer composition in order to provide increased elasticity. Use of elastin can permit slight circumferential expansion of the restrictive matrix in order to assist the tubular tissue, such as a vein, adapt to its new function, such as an arterial use. Elastin may be present in the polymer composition in any useful range, including without limitation, from about 2% wt. to about 50% wt., inclusive of all ranges and points therebetween, including from about 40% wt. and about 42.3% wt., inclusive of all integers and all points therebetween and equivalents thereof. In one non-limiting embodiment, collagen and elastin are present in approximately equal amounts in the polymer composition, In another embodiment, the sum of the collagen and elastin content in the polymer composition is in any useful range, including, without limitation, from about 2% wt. to about 95% wt., but more typically in the range of from about 25% wt. to about 75% wt., inclusive of all ranges and points therebetween, including from about 40% wt. to about 75% wt., including about 75% wt. and about 42.3% wt.

In one non-limiting embodiment, the polymer composition comprises a biodegradable poly(ester urethane) urea elastomer (PEUU). PEUU can be manufactured by reacting a diol with a diisocyanate to form a prepolymer and then reacting the prepolymer with a diamine. A non-limiting example of such a PEUU is an elastomeric polymer made from polycaprolactone diol ($M_W$ 2000) and 1,4-diisocyanatobutane, using a diamine chain extender such as putrescine. One non-limiting example or a method for preparing a PEUU polymer is a two-step polymerization process whereby polycaprolactone diol ($M_W$ 2000), 1,4-diisocyanatobutane, and diamine are combined in a 2:1:1 molar ratio. In the first step to form the prepolymer, a 15 wt % solution of 1,4-diisocyanatobutane in DMSO (dimethyl sulfoxide) is stirred continuously with a 25 wt % solution of polycaprolactone diol in DMSO. Then, stannous octoate is added and the mixture is allowed to react at 75° C. for 3 hours. In the second step, the prepolymer is reacted with a diamine to extend the chain and to form the polymer. In one embodiment, the diamine is putrescine, which is added drop-wise while stirring and allowed to react at room temperature for 18 hours. In one embodiment, the diamine is lysine ethyl ester, which is dissolved in DMSO with triethylamine, added to the prepolymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

In another non-limiting embodiment, the polymer composition comprises poly(ether ester urethane) urea elastomer (PEEUU). For example and without limitation, the PEEUU may be made by reacting polycaprolactone-b-polyethylene glycol-b-polycaprolactone triblock copolymers with 1,4-diisocyanatobutane and putrescine. In one non-limiting embodiment, PEEUU is obtained by a two-step reaction using a 2:1:1 reactant stoichiometry of 1,4-diisocyanatobutane:triblock copolymer:putrescine. According to one non-limiting embodiment, the triblock polymer can be prepared by reacting poly(ethylene glycol) and ε-caprolactone with stannous octoate at 120° C. for 24 hours under a nitrogen environment. The triblock copolymer is then washed with ethyl ether and hexane, then dried in a vacuum oven at 50° C. In the first step to form the prepolymer, a 15 wt % solution of 1,4-diisocyanatobutane in DMSO is stirred continuously with a 25 wt % solution of triblock copolymer in DMSO. Then, stannous octoate is added and the mixture is allowed to react at 75° C. for 3 hours. In the second step, putrescine is added drop-wise under stirring to the prepolymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

In another non-limiting embodiment, the polymer composition comprises a poly(ester carbonate)urethane urea (PECUU) or a poly(carbonate)urethane urea (PCUU), which are described, for example, in Hong et al. (Tailoring the degradation kinetics of poly(ester carbonate urethane)urea thermoplastic elastomers for tissue engineering scaffolds Biomaterials, Biomaterials 31 (2010) 4249-4258). Poly(ester carbonate urethane)urea (PECUU) is synthesized, for example using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and PHC (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of Sn(Oct)$_2$. The flask is placed in an oil bath at 70° C. After 3 h, the prepolymer solution is cooled at room temperature and then a putrescine/DMSO solution is added dropwise into the agitated solution. The final polymer solution concentration is controlled to be approximately 4% (w/v). Then the flask is than placed in an oil bath and kept at 70° C. overnight. The polymer is precipitated in an excess volume of cool deionized water and then dried in a vacuum at 60° C. for 3 days. The polyurethane ureas synthesized from the different PCL/PHC molar ratios defined above are referred to as PEUU, PECUU 75/25, PECUU 50/50, PECUU 25/75 and PCUU, respectively. In practice, the yields of all final products using this method is approximately 95%.

As indicated above, diamines and diols are useful building blocks for preparing the (co)polymer compositions described herein. Diamines as described above have the structure H$_2$N—R—NH$_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as polycaprolactone-PEG copolymers, including polycaprolactone-b-polyethylene glycol-b-polycaprolactone triblock copolymers of varying sizes. Other building blocks for useful diols include, without limitation glycolides (e.g. polyglycolic acid (PGA)), lactides, dioxanones, and trimethylene carbonates. Diisocyanates have the general structure OCN—R—NCO, where "R" is an aliphatic or aromatic hydrocarbon or a hydrocarbon comprising aromatic and aliphatic regions. The hydrocarbon may be linear or branched.

In additional embodiments, the polymer composition comprises polyethylene terephthalate (PET, e.g., DACRON). Of note, PET is less biodegradable than the copolymers described above, and is stiffer. PET scaffolds structures are made essentially in the manned described herein for PEUU and other polymer compositions described herein. Polymer concentrations and infusion rates may be altered to accommodate the different qualities of the PET composition, for example and without limitation, for PET, 20% w/v in HFIP at 12 mL/h infusion rate, as used in the examples below.

In other embodiments, the polymer composition comprises a tyrosine polyarylate (TPA). As with PET, TPA is less biodegradable than the polyurethane copolymers described above, and also is stiffer. TPA scaffolds structures are made essentially in the manned described herein for PEUU and other polymer compositions. Polymer concentrations and infusion rates may be altered to accommodate the different qualities of the TPA composition, for example and without limitation, for TPA, 12% w/v in HFIP at 20 mL/h infusion rate, as used in the examples below. Tyrosine polyarylates are commonly prepared from an aliphatic acid and a tyrosine-derived diphenol. Non-limiting examples of useful aliphatic acids include: succinic acid, adipic acid, sebacic acid, and dicarboxylic acid chlorides or anhydrides. Non-limiting examples of tyrosine-derived diphenols include desaminotyrosyl-tyrosine alkyl esters, where the alkyl is, for example, one of ethyl, hexyl and octyl) (DTE). As an example, in the Examples below, Poly(DTE-co-27.5 DT succinate) was used. TPAs and methods of making TPAs are described, for example, in U.S. Pat. No. 5,216,115 and United States Patent Publication No. 2011/0082545, each of which is incorporated herein by reference for its technical disclosure, disclose useful TPAs. Additional references disclosing TPA compositions and methods of making and using those compositions include: Fiordeliso, J, et al. (1994) Design, synthesis, and preliminary characterization of tyrosine-containing polyarylates: new biomaterials for medical applications, *J Biomater Sci Polym Ed.* 1994; 5(6):497-510; Huang, X et al. (2009) A library of L-tyrosine-derived biodegradable polyarylates for potential biomaterial applications, part I: synthesis, characterization and accelerated hydrolytic degradation *J Biomater Sci Polym Ed.* 2009; 20(7-8):935-55; and Bourke, S L et al. (2003) Polymers derived from the amino acid L-tyrosine: polycarbonates, polyarylates and copolymers with poly(ethylene glycol) *Adv Drug Deliv Rev.* 2003 Apr. 25; 55(4):447-66.

In another embodiment, at least one therapeutic agent is added to the scaffold or composition described herein before it is implanted in the patient or otherwise administered to the patient. Generally, the therapeutic agents include any substance that can be coated on, embedded into, absorbed into, adsorbed to, or otherwise attached to or incorporated onto or into the structure or incorporated into a drug product that would provide a therapeutic benefit to a patient. Non-limiting examples of such therapeutic agents include antimicrobial agents, growth factors, emollients, retinoids, and topical steroids. Each therapeutic agent may be used alone or in combination with other therapeutic agents. For example and without limitation, a structure comprising neurotrophic agents or cells that express neurotrophic agents may be applied to a wound that is near a critical region of the central nervous system, such as the spine. Alternatively, the therapeutic agent may be blended with the polymer while a polymer is being processed. For example, the therapeutic agent may be dissolved in a solvent (e.g., DMSO) and added to the polymer blend during processing. In another embodiment, the therapeutic agent is mixed with a carrier polymer (e.g., polylactic-glycolic acid microparticles) which is subsequently processed with an elastomeric polymer. By blending the therapeutic agent with a carrier polymer or elastomeric polymer itself, the rate of release of the therapeutic agent may be controlled by the rate of polymer degradation.

In certain non-limiting embodiments, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting embodiments, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting embodiments, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin. Other drugs that may promote wound healing and/or tissue regeneration may also be included.

Structures described herein are preferably made by electrospinning of the biodegradable, elastomeric polymer, and concurrent deposition of the ECM gel, and/or where appropriate a blood product or other liquid, by spraying, e.g., electrospraying. Other compounds or components may be incorporated into a structure as described herein by any method, including absorption, adsorption, mixing, etc.

The deposited biodegradable, elastomeric polymer typically is porous. As used herein, the term "porosity" refers to a ratio between a volume of all the pores within the polymer composition and a volume of the whole polymer composition. For instance, a polymer composition with a porosity of 85% would have 85% of its volume containing pores and 15% of its volume containing the polymer. In certain non-limiting embodiments, the porosity of the structure is at least 60%, 65%, 70%, 75%, 80%, 85%, or 90%, or increments therebetween. In another non-limiting embodiment, the average pore size of the structure is between 0.1 and 300 microns, 0.1 and 100 microns, 1-25 microns, including increments therebetween. For example and without limitation, a structure that acts as a barrier to bacteria and other pathogens may have an average pore size of less than 0.5 microns or less than 0.2 microns. The structures described herein are manufactured by electrospinning. It therefore is often advantageous to adjust the pore size or degree of porosity by varying the polymer concentration of the electrospinning solution or by varying the spinning distance from the nozzle to the target. For example and without limitation, the average pore size may be increased by increasing the amount of polymeric components within the suspension used for electrospinning, which results in larger fiber diameters and therefore larger pore sizes. In another non-limiting example, the average pore size can be increased by increasing spinning distance from the nozzle to the target, which results in less adherence between fibers and a looser matrix. Where ECM gel is co-deposited during the electrospinning, many of the pores (that is a large percentage of the pores or interstices) in the deposited polymer are filled with the ECM gel.

In certain preferred embodiments, electrospinning is used to deposit the biodegradable, elastomeric polymer and optionally the ECM gel and/or other liquid, such as a mammalian blood product, media buffer solution, medium, etc. In its simplest sense, electrospinning is caused by the deposit of a liquid composition, such as polymer fibers onto a target surface caused by an electric potential. Electrospinning methods are well-known in the field of tissue engineering and are conducted essentially as described below. Electrospinning permits fabrication of structures that resemble the scale and fibrous nature of the native extracellular matrix (ECM). The ECM is composed of fibers, pores, and other surface features at the sub-micron and nanometer size scale. Such features directly impact cellular interactions with synthetic materials such as migration and orientation. Electrospinning also permits fabrication of oriented fibers to result in structures with inherent anisotropy. These aligned structures can influence cellular growth, morphology and ECM production. For example, Xu et al. found smooth muscle cell (SMC) alignment with poly(L-lactide-co-ε-caprolactone) fibers [Xu C.Y., Inai R., Kotaki M., Ramakrishna S., "Aligned biodegradable nanofibrous structure: a potential for blood vessel engineering", Biomaterials 2004 (25) 877-86.] and Lee et al. submitted aligned non-biodegradable polyurethane to mechanical stimulation and found cells cultured on aligned scaffolds produced more ECM than those on randomly organized scaffolds [Lee C. H., Shin H. J., Cho I. H., Kang Y. M. Kim I. A., Park K. D., Shin, J. W., "Nanofiber alignment and direction of mechanical strain affect the ECM production of human ACL fibroblast", Biomaterials 2005 (26) 1261-1270].

The process of electrospinning involves placing a polymer-containing fluid (for example, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (typically a collector screen or rotating mandrel). During electrospinning, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (for example, 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh is formed on the biased target. Under certain conditions, for instance with solutions lacking sufficient viscosity and/or electrospun with certain tolerances, a fiber is not formed, but a spray is formed, depositing discrete droplets onto the target instead of a fiber. This is electrospraying.

The properties of the electrospun structures, e.g., elastomeric scaffolds, can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain non-limiting embodiments, the biased target is moved back and forth in a regular, periodic fashion, such that fibers of the non-woven mesh are substantially parallel to each other. When this is the case, the resulting non-woven mesh may have a higher resistance to strain in the direction parallel to the fibers, compared to the direction perpendicular to the fibers. In other non-limiting embodiments, the biased target is moved randomly relative to the orifice, so that the resistance to strain in the plane of the non-woven mesh is isotropic. The target can also be electrospun on a rotating mandrel. In this case, the properties of the non-woven mesh may be changed by varying the speed of rotation. The properties of the electrospun structure may also be varied by changing the magnitude of the voltages applied to the electrospinning system. In one non-limiting embodiment, the electrospinning apparatus includes an orifice biased to 12 kV, a target biased to −7 kV, and a focusing ring biased to 3 kV. Moreover, a useful orifice diameter is 0.047" (I.D.) and a useful target distance is about 23 cm. Other electrospinning conditions that can be varied include, for example and without limitation, the feed rate of the polymer solutions, the solution concentrations, and the polymer molecular weight.

In certain embodiments, electrospinning is performed using two or more nozzles, wherein each nozzle is a source of a different polymer solution. The nozzles may be biased with different biases or the same bias in order to tailor the physical and chemical properties of the resulting non-woven polymeric mesh. Additionally, many different targets may be used. In addition to a flat, plate-like target, use of a mandrel or a revolving disk as a target is contemplated.

When the electrospinning is to be performed using a polymer suspension, the concentration of the polymeric component in the suspension can also be varied to modify the physical properties of the elastomeric scaffold. For example, when the polymeric component is present at relatively low concentration, the resulting fibers of the electrospun non-woven mesh have a smaller diameter than when the polymeric component is present at relatively high concentration. Without wishing to be limited by theory, it is believed that lower concentration solutions have a lower viscosity, leading to faster flow through the orifice to produce thinner fibers. One skilled in the art can adjust polymer concentrations to obtain fibers of desired characteristics. Useful ranges of concentrations for the polymer component are from 1 wt % to 25 wt %, 4 wt % to 20 wt %, and from 10 wt % to 15 wt %, including increments therebetween for all ranges.

In one non-limiting embodiment, the structure is produced by co-electrospinning a polymer suspension comprising a synthetic polymeric component and a biological polymeric component, along with electro spraying the ECM gel and/or other liquid. In another non-limiting embodiment, the polymeric component of the structure is produced by electrospinning a polymer suspension comprising a synthetic polymeric component from one nozzle and a polymer suspension comprising a biological polymeric component from another nozzle. Non-limiting examples of useful range of high-voltage to be applied to the polymer suspension is from 0.5 to 30 kV, from 5 to 25 kV, and from 10 to 15 kV.

The ECM gel component of the structure is sprayed (e.g. pressure sprayed) or electrosprayed concurrently with the electrospinning of the polymer(s). Likewise, the liquid component of the wet-electrospun layer(s) is sprayed or electrosprayed concurrently with the polymeric constituents.

Figure 2:
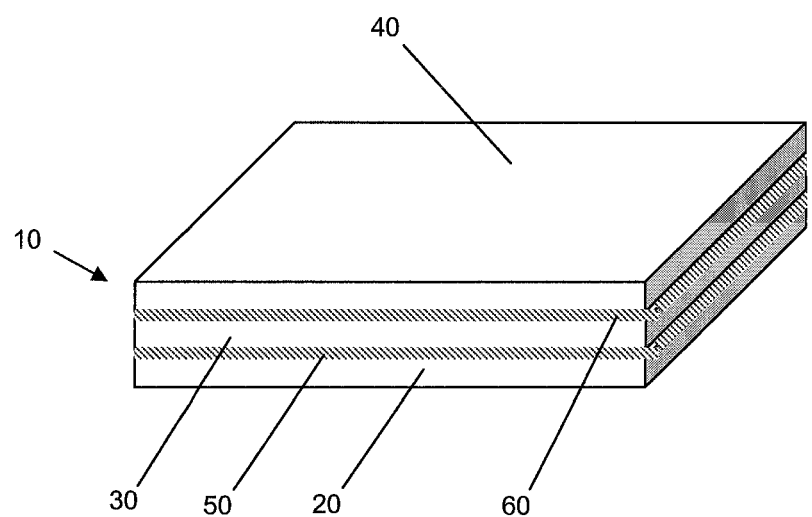
FIG. 2 is a schematic depiction of a three-layer scaffold structure as described herein.

In one embodiment, a multi-layer structure is produced. FIG. 2 depicts a three-layer structure 10. The structure 10 comprises a first layer 20 of a wet-electrospun biodegradable elastomeric polymer composition, comprising a biodegradable, biocompatible elastomeric polymer composition and a liquid, such as an aqueous liquid, for example and without limitation a liquid selected from one or more of water, a physiological salt solution, a buffer solution, a mammalian blood product or cell culture medium. The structure 10 comprises a second layer 30 attached to the first layer 20, comprising a biodegradable elastomeric polymer composition and an ECM gel. The structure also comprises a third layer 40 attached to the second layer 30 opposite the first layer 20, comprising a biodegradable elastomeric polymer composition and a liquid, such as an aqueous liquid, for example and without limitation a liquid selected from one or more of water, a physiological salt solution, a buffer solution, a mammalian blood product or cell culture medium. The first layer 20 and second layer 30 are attached at a first interlayer 50 and the second layer 30 and third layer 40 are attached at a second interlayer 60. The first layer 20 and the third layer 40 may be the same or different, comprising the same biodegradable elastomeric polymer composition and/or a liquid, such as an aqueous liquid, for example and without limitation a liquid selected from one or more of water, a physiological salt solution, a buffer solution, a mammalian blood product and cell culture medium or different biodegradable elastomeric polymer composition and/or a liquid, such as an aqueous liquid, for example and without limitation a liquid selected from one or more of water, a physiological salt solution, a buffer solution, a mammalian blood product and cell culture medium. The second layer 30 may comprise the same biodegradable elastomeric polymer composition as the first layer 20 and/or the third layer 40.

Because the multi-layered structure 10 of FIG. 2 is produced by electrospinning, the interlayers 50 and 60 comprise fibers of both the adjacent layers, a number of which are interlocked or intertwined, or can be continuous between layers. In one embodiment, the biodegradable elastomeric polymer composition is deposited continuously from the first layer 20 through the third layer 40. While the biodegradable elastomeric polymer composition is deposited continuously, the liquid, such as an aqueous liquid, for example and without limitation a liquid selected from one or more of water, a physiological salt solution, a buffer solution, a mammalian blood product and cell culture medium is first deposited, producing the first layer, then the ECM gel is deposited, producing the second layer 30, and lastly the liquid, such as an aqueous liquid, for example and without limitation a liquid selected from one or more of water, a physiological salt solution, a buffer solution, a mammalian blood product and cell culture medium is deposited, producing the third layer 40. In this embodiment, the biodegradable elastomeric polymer composition is the same throughout the structure 10, and the liquid, such as an aqueous liquid, for example and without limitation a liquid selected from one or more of water, a physiological salt solution, a buffer solution, a mammalian blood product and cell culture medium is the same in the first and third layers, 20 and 40. In this particular electrospinning process, three reservoirs are used: one containing the biodegradable elastomeric polymer composition, one containing the liquid, such as an aqueous liquid, for example and without limitation a liquid selected from one or more of water, a physiological salt solution, a buffer solution, a mammalian blood product and cell culture medium, and one containing the ECM gel. Alternately, additional reservoirs can be used in order to change one or more ingredients in each layer. For example two reservoirs, each comprising a different biodegradable elastomeric polymer composition may be used for deposition of two adjacent layers, and in order to increase adhesion between layers the first biodegradable elastomeric polymer composition is deposited followed by the second, with a period of time during deposition in which both are deposited, resulting in an interlayer comprising both biodegradable elastomeric polymer compositions. Flow of materials from the reservoirs may be controlled manually or by computer.

In one alternate embodiment to that of FIG. 2, the third layer 40 and therefore the second interlayer 60 are omitted producing a structure of two layers. Likewise, additional layers or interlayers may be included in the structure, yielding a structure of four or more layers. Additional ingredients, such as therapeutic agents or cells as described herein, can be deposited, e.g., by electrospraying, onto or within one or more layers.

The multi-layered structure, for example as illustrated in FIG. 2, combines a biodegradable elastomeric polymer composition and an ECM gel, with one or more physically stronger layers of a wet-electrospun biodegradable elastomeric polymer composition. The wet-electrospun stronger layers have a lower amount of the ECM gel material than the layer(s) comprising the biodegradable elastomeric polymer composition and the ECM gel material, and in certain embodiments omit the ECM gel material. As an example, the multi-layered structure comprises a layer of the combined polymer/ECM material between two layers of wet-electrospun biodegradable elastomeric polymer composition essentially as shown in FIG. 2. Examples of wet-electrospun biodegradable elastomeric polymer compositions are described in International Patent Application No. PCT/US2011/038332, filed May 27, 2011, incorporated herein by reference in its entirety. Suitable biodegradable elastomeric polymer compositions for wet-electrospinning are described herein as the biodegradable elastomeric polymer composition described above, which may comprise a biological polymer component, though typically not an ECM gel. Therefore according to one embodiment, a composition is produced comprising a first layer of a wet-electrospun biodegradable elastomeric polymer composition, a second layer of a biodegradable elastomeric polymer composition co-deposited with an ECM gel and a third layer on an opposite side of the second layer from the first layer of a wet-electrospun biodegradable elastomeric polymer composition that is the same or different than the wet-electrospun biodegradable elastomeric (co)polymer of the first layer.

The wet-electrospun layers are "wet electrospun," meaning a liquid, such as an aqueous liquid, for example and without limitation a liquid selected from one or more of water, a physiological salt solution, a buffer solution, a mammalian blood product or cell culture medium, such as a serum-containing liquid or a mammalian blood product, is deposited as the polymer is electrospun. One method would be to spray the liquid at the same time the polymer is electrospun. In one embodiment, the liquid is electrosprayed in substantially the same manner as the polymer is electrospun, the only difference being the deposited liquid is less viscous than the polymer, and the potential difference is such that droplets, rather than fibers are deposited. In one embodiment, the liquid is serum in normal saline, PBS, cell culture medium or a balanced salt solution, optionally comprising other additives. In the example below, the electrosprayed medium is Dulbecco's Modified Eagle Medium (DMEM) with 10% fetal bovine serum (FBS), 10% horse serum, 1% penicillin/streptomycin, and 0.5% chick embryo extract. As can be recognized by those of ordinary skill in the relevant arts, there are a multitude of salt solutions, buffered salt solutions, media, media supplements, active agents, such as antibiotics, growth factors and cytokine, biopolymers and ECM-derived material that would serve equally as a substitute for the electrosprayed serum-containing liquids described in the examples below. Compositions that are do not include blood products are referred to herein as physiological solutions, which are biocompatible, aqueous solutions, including salt solutions and blood-product-free medium, though blood products can be added to the physiological solutions. Other potentially useful media include, without limitation: DMEM, MEM, RPMI 1640, F10, OptiMEM, serum-free media, EMEM, EBM-2, F12, IMDM, and Media 199 (available, e.g., from Invitrogen). Salt solutions may be used instead of media, such as, without limitation: saline, normal saline (approximately 0.9% (w/v)), Dulbecco's phosphate-buffered salines, Hanks' balanced salt solutions, phosphate buffered salined or Earle's balanced salt solutions. Media supplements include, without limitation: HEPES, Calcium chloride, or sodium bicarbonate. Antibiotics include, without limitation: actinomycin D, ampicillin, carbenicillin, cefotaxime, fosmidomycin, gentamycin, kanmycin, neomycin, penicillin streptomycin, polymyxin B and streptomycin. Mixtures of more than one media, supplement, or antibiotic can also be used.

According to one embodiment, the electrosprayed liquid comprises one or more xenogeneic, allogeneic, isogeneic, syngeneic or autologous blood products, such as serum, plasma or platelet-rich plasma. "Serum" is a cell-free, fibrinogen-free blood fraction. In one non-limiting embodiment, an aliquot of a patient's blood is removed and serum is prepared from the blood by allowing the blood to clot and removing the clotted material and cellular material, typically by first "ringing" the sample, and then by centrifugation. Plasma is made by centrifuging a tube of fresh blood containing an anti-coagulant in a centrifuge until the blood cells fall to the bottom of the tube. Platelet Rich Plasma is defined as a volume of the plasma fraction of autologous blood having a platelet concentration above baseline. (See, generally, Sampson et al. Curr Rev Musculoskelet Med. 2008 December; 1(3-4):165-74). One method of preparing platelet-rich plasma is by density-gradient centrifugation and collection of the buffy coat. A device, such as the Biomet Biologics GPS III device can be used to obtain a platelet rich plasma fraction. Platelet-rich buffy coat preparations can be mixed with plasma, serum, saline, PBS or any suitable salt, buffer, media, etc.

For either the wet-electrospun layer(s) or the ECM gel-containing layers, stabilizing compositions, such as stabilizing proteins may be included in the electrosprayed liquid composition. Likewise viscosity enhancers, including, without limitation: polymeric compounds may also be added.

Allogeneic blood fractions, such as one or more of serum, plasma or platelet-rich plasma, may be used. An electrospray liquid to be concurrently electrosprayed during electrospinning of the polymer component of the matrices described herein may comprise blood fraction (e.g., serum, plasma or platelet-rich plasma, or mixtures thereof) concentrations ranging from approximately 1% to 100%, including any increment therebetween, such as 1%, 5%, 10%, 20%, 30%, 40%, 50%, 60%, 70%, 80%, 90% and 100% and any increment therebetween. In one embodiment, the electrospray liquid comprises from 5%-25% autologous or allogeneic blood product(s), and in another embodiment, 20%. When the blood fraction(s) is not 100% of the electrospray liquid, the electrospray liquid will comprise a suitable aqueous liquid, such as water, normal saline, PBS, or a cell culture medium as described above. As described elsewhere herein, the electrospray liquid also may comprise antibiotics, buffers, active agents, growth factors, cytokines, biopolymers, ECM derived material etc. in appropriate concentrations.

Because the electrospinning process may be controlled either manually or by computer, different ratios of polymer and electrosprayed liquid may be deposited in different layers of the matrix. For example, the ratio of liquid to polymer may increase in regions of the matrix where it is desirable to get increased cell infiltration, though too much liquid could lead to polymer delamination.

The materials made by the methods described herein may be sterilized by any useful means, and then packaged and distributed, e.g., according to standard usage in the biomedical industry. In use, the structures described herein can be used for cell growth and implantation for tissue generation or regeneration. For example, sheets of the structures can be used to replace skin or abdominal wall tissue. The sheets can be sutured, glued or otherwise affixed into place. Because the structures biodegradable, it is gradually replaced by native-origin tissue. If formed into a tubular structure, it may be used to replace blood vessels or portions of a patient's digestive tract and implanted, e.g., by anastomosis. It can also be used as a reinforcement for tissue already present in the patient. As seen herein, damage to an abdominal wall can be repaired by suturing the scaffold into remaining abdominal wall tissue, preferably to completely replace abdominal wall tissue removed or damaged. The scaffolds also may be used in vitro, in any suitable cell growth vessel, bioreactor, plate, flask, etc. In one embodiment, prior to implantation, the scaffold is placed in a cell culture vessel with media and cells of a patient, and the cells are allowed to grow on, and infiltrate within the scaffold prior to implantation. In another embodiment, the scaffold is placed within a patient and after a desired period of time for cell infiltration, explanted and re-implanted at a different location.

In another embodiment, the cells of interest are dissolved into an appropriate solution (e.g., a growth medium, buffer, or even the ECM gel electrosprayed during formation of the scaffold) and then sprayed onto a biodegradable elastomeric scaffold while the scaffold is being formed by electrospinning. This method is particularly suitable when a highly cellularized tissue engineered construct is desired. While pressure spraying (that is, spraying cells from a nozzle under pressure) is contemplated herein, in certain non-limiting embodiments, the cells are electrosprayed onto the non-woven mesh during electrospinning. As described herein, electrospraying involves subjecting a cell-containing solution with an appropriate viscosity and concentration to an electric field sufficient to produce a spray of small charged droplets of solution that contain cells.

EXAMPLES

The objective of these studies is to identify a biomaterial for use in development of a biohybrid device combining the biomechanical properties of synthetic scaffold materials with the biochemical features of natural acellular scaffold devices. These materials will find use in reconstruction of tissues and structures that require good physical strength, such as in pelvic floor or abdominal wall replacement. This requires analysis of: mechanical properties of the biomaterials; in vitro and in vivo biocompatibility of the materials; and in vivo host response evaluation in a rodent model.

The biodegradable thermoplastic elastomer poly(ester urethane) urea (PEUU), prepared essentially as described by co-polymerization of polycaprolactone diol (Mw 2000) and 1,4-diisocyanobutane at 70° in the presence of $Sn(OCt)_2$ (stannous octoate or Tin 2-Ethylhexanoate) to produce a prepolymer and then reacting the prepolymer with putrescine ($H_2N(CH_2)_4NH_2$) (Guan J J, et al. Synthesis, characterization, and cytocompatibility of elastomeric, biodegradable poly(ester-urethane)ureas based on poly(caprolactone) and putrescine. J Biomed Mater Res. 2002; 61:493-503).

Dermal ECM gel is prepared from porcine dermis as follows. Frozen samples of porcine dermis were thawed at room temperature and cut into smaller sized pieces. The tissue samples were subject to a series of washes for enzymatic decellularization (trypsin washes), osmotic lysis ($dH_2O$ washes), sterilization (ethanol), peroxide washes, aqueous washes (1% Triton X-100 in EDTA/Trizma), disinfection (peracetic acid), and final aqueous washes. Acellular samples were lyophilized and comminuted into powder form. Powdered dECM was subject to enzymatic digest (pepsin) for 48 hours. dECM digest solutions are adjusted in concentration and osmotic strength to yield a working gelling solution of neutral pH at 10 mg/ml and used immediately for the preparation of PEUU/dECM biohybrid devices by co-electrospinning.

Figure 3:
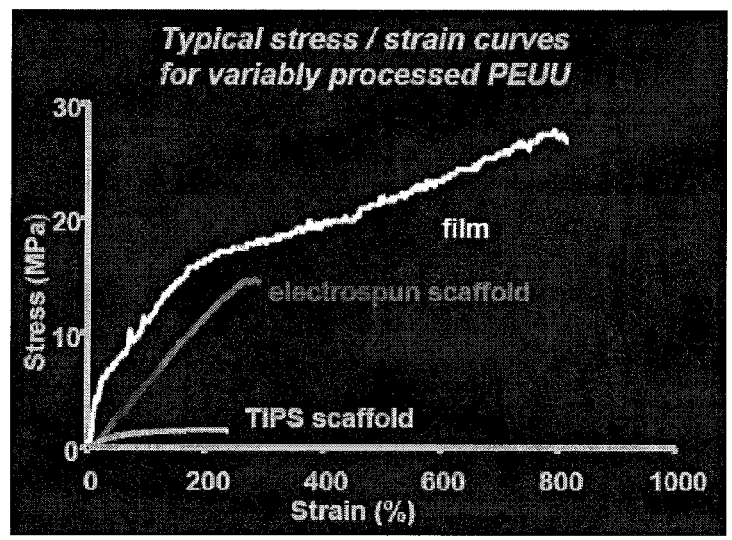
FIG. 3 is a graph depicting mechanical properties of a PEUU prepared either as a film, a TIPS scaffold or electrospun.

Electrospinning is conducted either onto a non-rotating surface or onto a spinning mandrel, as described above. FIG. 3 depicts mechanical properties of PEUU by itself prepared either as a film, a TIPS scaffold or electrospun. Table A provides additional physical properties of those materials.

TABLE A

| Polymer | Processing | Tensile Strength (mPa) | Breaking Strain (%) |
|---|---|---|---|
| PEUU | Film | 27 ± 4 | 820 ± 70 |
| PEUU | TIPS | 1.5 ± .02 | 200 ± 60 |
| PEUU | Electrospun | 13 ± 4 | 220 ± 80 |

Scaffolds manufactured from PEUU and solubilized UBM, and post-implantation histology of those scaffolds may be prepared essentially as described in Stankus et al., Hybrid nanofibrous scaffolds from electrospinning of a synthetic biodegradable elastomer and urinary bladder matrix, J. Biomater. Sci. Polym. Ed. (2008) 19(5):635-652, that is by blending PEUU and ECM material an electrospinning in a single stream. While that process is effective to some extent for certain purposes, scaffolds prepared in that manner are not optimal.

The scaffolds prepared according to the methods described herein are superior because they combine the benefits of two excellent scaffold materials to yield a much superior product. Electrospun elastomeric scaffolds have the benefit of elasticity, biodegradation, good mechanical behavior (e.g., surgical handling) and controllable mechanical properties, but negatives include poor cellular infiltration and, depending on the polymer composition, foreign body response prior to complete degradation. Dermal ECM hydrogels have the benefit of good biocompatibility and cell and tissue chemoattraction, but negatives include weak mechanical properties, poor control of mechanical properties and fast degradation. The benefits of the combined polymer/ECM gel material include: superior tissue mimetic, good biodegradation rates, elasticity, good cellular infiltration, adequate to excellent mechanical support and adequate to good surgical handling.

In the experiments described below, the polymer/ECM gel is formed by electrospinning PEUU as described above, onto a spinning mandrel and concurrently electrospraying dermal ECM onto the scaffold, as described below. Once formed, the scaffold is cut off the mandrel and heated to 37° C. to cause the ECM material to gel.

Example 1

A hybrid scaffold (PEUU/dECM=50/50) was prepared from PEUU, prepared as described above and dermal ECM (dECM) prepared as described above. The scaffolds were formed by concurrent electrospinning of the PEUU and electrospraying of the dECM material. 10 mL dermal ECM gel solution (10 mg/ml) was fed by a syringe pump at 1.5 mL/min into a sterilized capillary (1.2 mm inner diameter) charged at 7 kV and suspended 4 cm above the target mandrel (19 mm diameter). Concurrently, PEUU in hexafluoroisopropanol solution (10%, w/v) was fed at 10 mL/h from a capillary, charged at 12 kV and perpendicularly located 20 cm from the target mandrel. The mandrel was charged at −4 kV and rotated at 250 rpm (8 cm/s tangential velocity) while translating back and forth 8 cm along the x-axis at 0.15 cm/s. After processing, PEUU/gel solution hybrid was cut off from mandrel using a blade and then was immediately placed in an incubator at 37° C. After 2 h, dECM gel solution completely formed a solid gel and PEUU/dECM gel hybrid scaffold was obtained.

Figure 4:
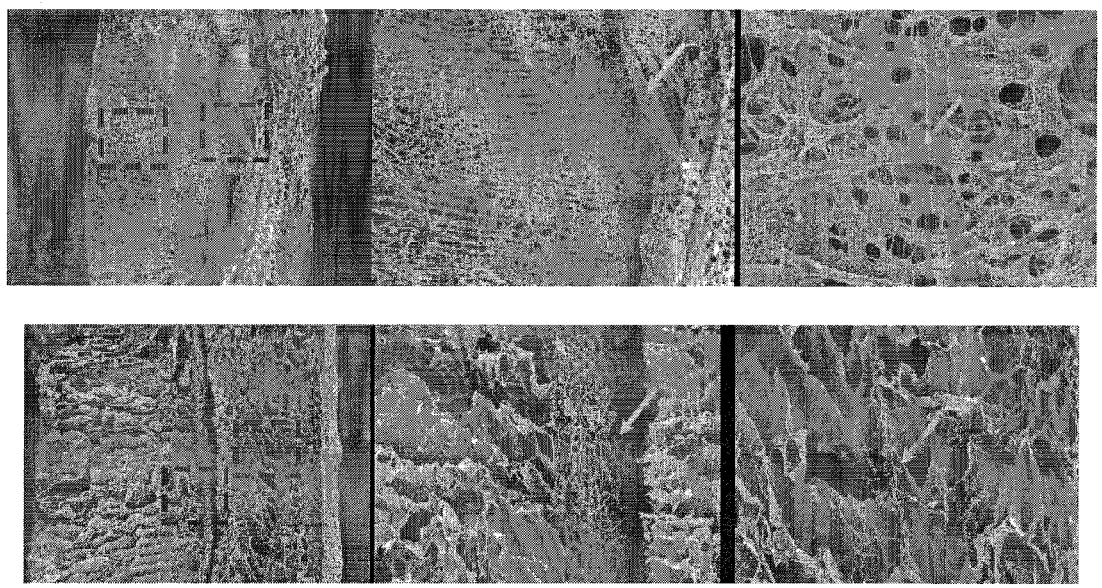
FIG. 4 are photomicrographs showing cross-section morphology of a PEUU/dECM hybrid scaffold (50:50).
Figure 5:
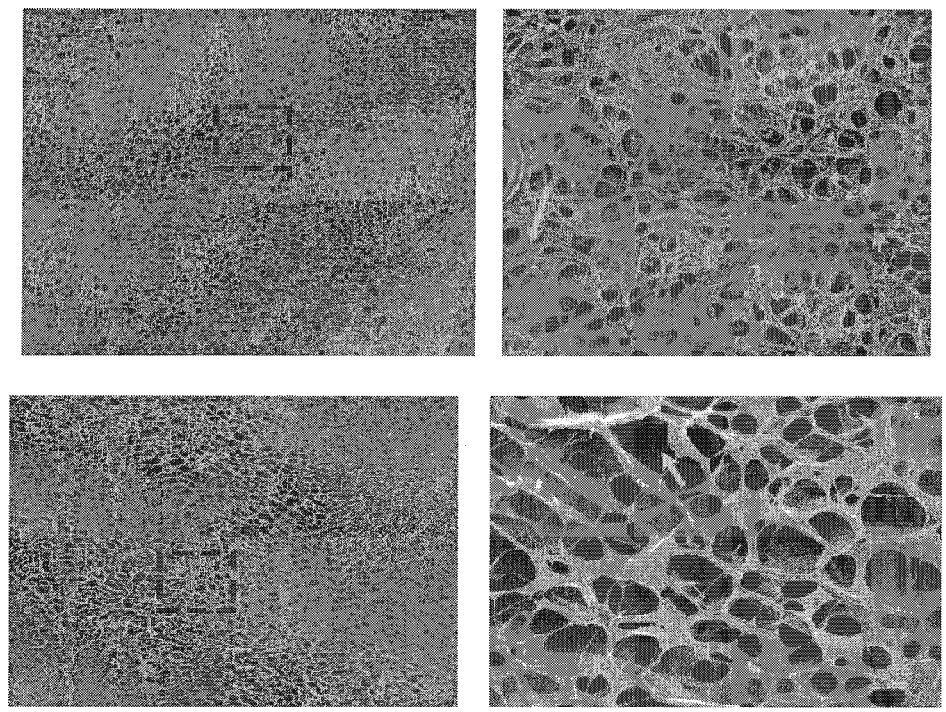
FIG. 5 are photomicrographs showing surface morphology of a PEUU/dECM hybrid scaffold (50:50).
Figure 6A:
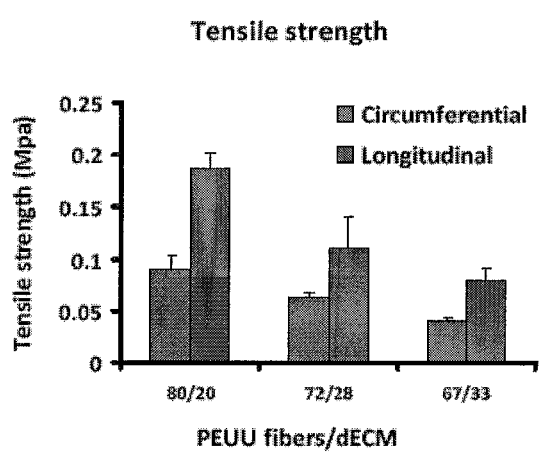
FIGS. 6A and 6B are graphs showing mechanical properties of PEUU/dECM hybrid scaffolds at different PEUU/dECM ratios, which were tuned by changing gel feeding rate (6A—tensile strength, 6B—strain at maximum stress).
Figure 6B:
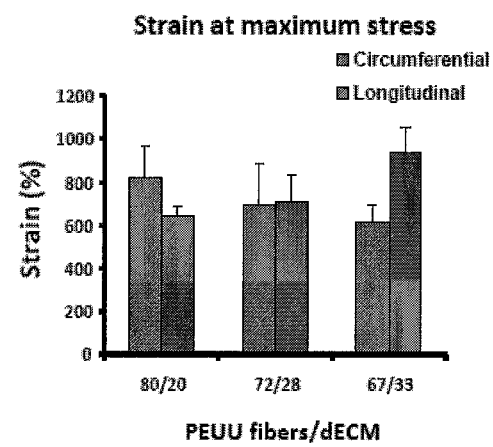

FIG. 4 shows cross-section morphology of the PEUU/dECM hybrid scaffold (50:50). FIG. 5 shows surface morphology of the PEUU/dECM hybrid scaffold (50:50). It was observed that the fiber/gel microstructure of PEUU/dECM gel hybrid scaffold forms a multilammelar structure with fibers extending between the layers. The resultant material is easily handled and is elastic. FIGS. 6A and 6B provide graphs showing mechanical properties of PEUU/dECM hybrid scaffolds at different PEUU/dECM ratios, which were tuned by changing gel feeding rate.

10 mL dermal ECM gel solution (10 mg/ml) was fed by a syringe pump at 1, 1.5 or 2 mL/min into a sterilized capillary (1.2 mm inner diameter) charged at 7 kV and suspended 4 cm above the target mandrel (19 mm diameter). Concurrently, PEUU in hexafluoroisopropanol solution (12%, w/v) was fed at 20 mL/h from a capillary, charged at 12 kV and perpendicularly located 20 cm from the target mandrel. The mandrel was charged at −4 kV and rotated at 250 rpm (8 cm/s tangential velocity) while translating back and forth 8 cm along the x-axis at 0.15 cm/s. After processing, PEUU/gel solution hybrid was cut off from mandrel using a blade and then was immediately placed in an incubator at 37° C. After 2 h, dECM gel solution completely formed a solid gel. Three different hybrid scaffolds at PEUU/dECM ratios of 80/20, 72/28, and 67/33 were obtained when gel solution feeding rates were 1, 1.5 and 2 ml/min, respectively.

Figure 7:
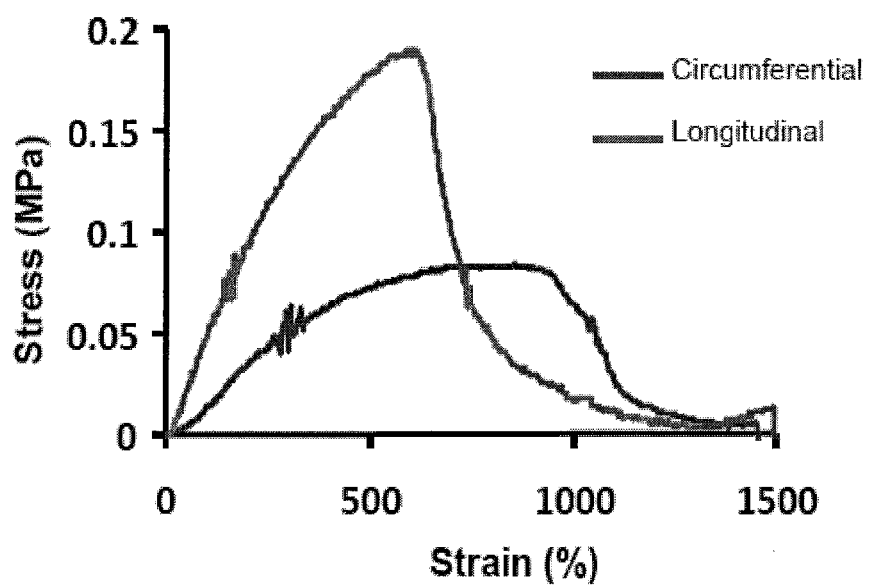
FIG. 7 is a graph depicting typical stress-strain curves of a PEUU/dECM gel hybrid scaffold (80/20) at longitudinal and circumferential directions.

A strip sample was cut from PEUU/dECM hybrid scaffold at longitudinal or circumferential direction. Uniaxial mechanical properties of such sample were measured on an MTS Tytron 250 MicroForce Testing Workstation at room temperature. The crosshead speed was set at 1 inch/min according to ASTM D638-98. FIG. 7 depicts typical stress-strain curves of PEUU/dECM gel hybrid scaffold (80/20) at longitudinal and circumferential directions.

Example 2

Figure 8:
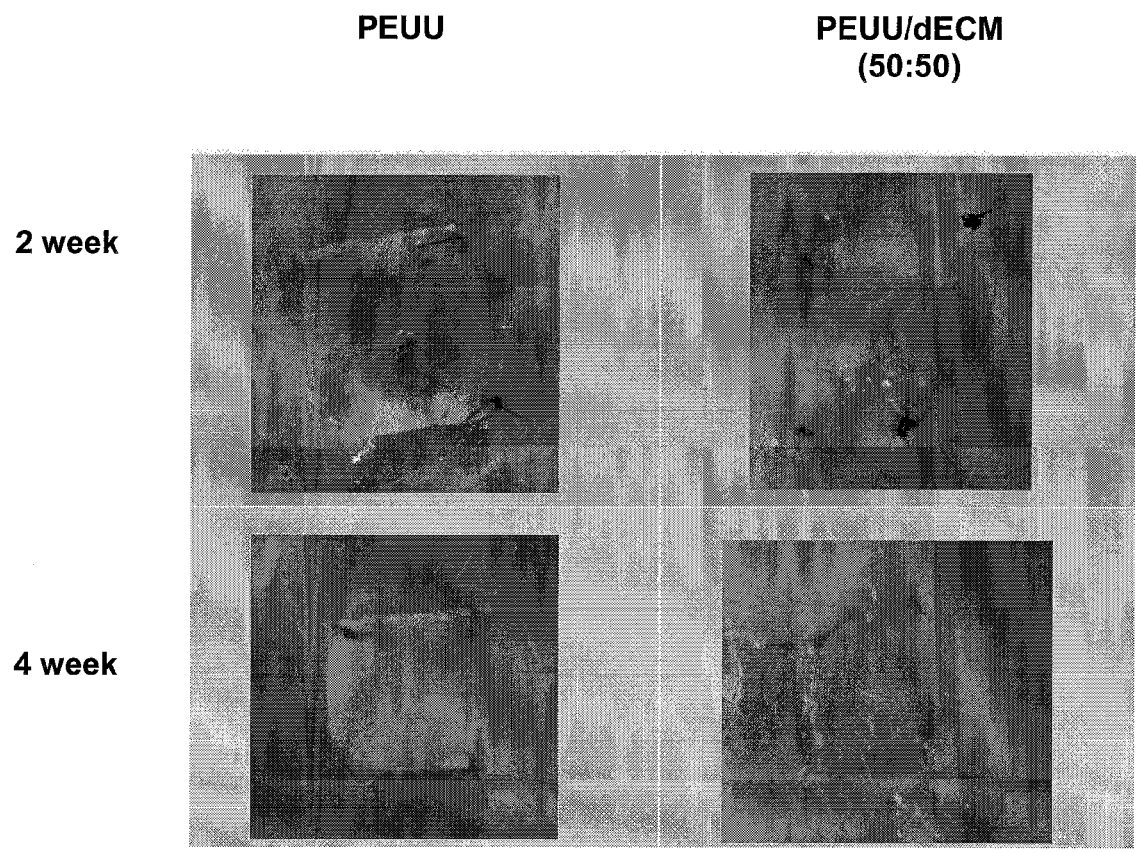
FIG. 8 provides photographs showing macroscopic images of implants at two and four weeks post-implant.
Figure 9A:
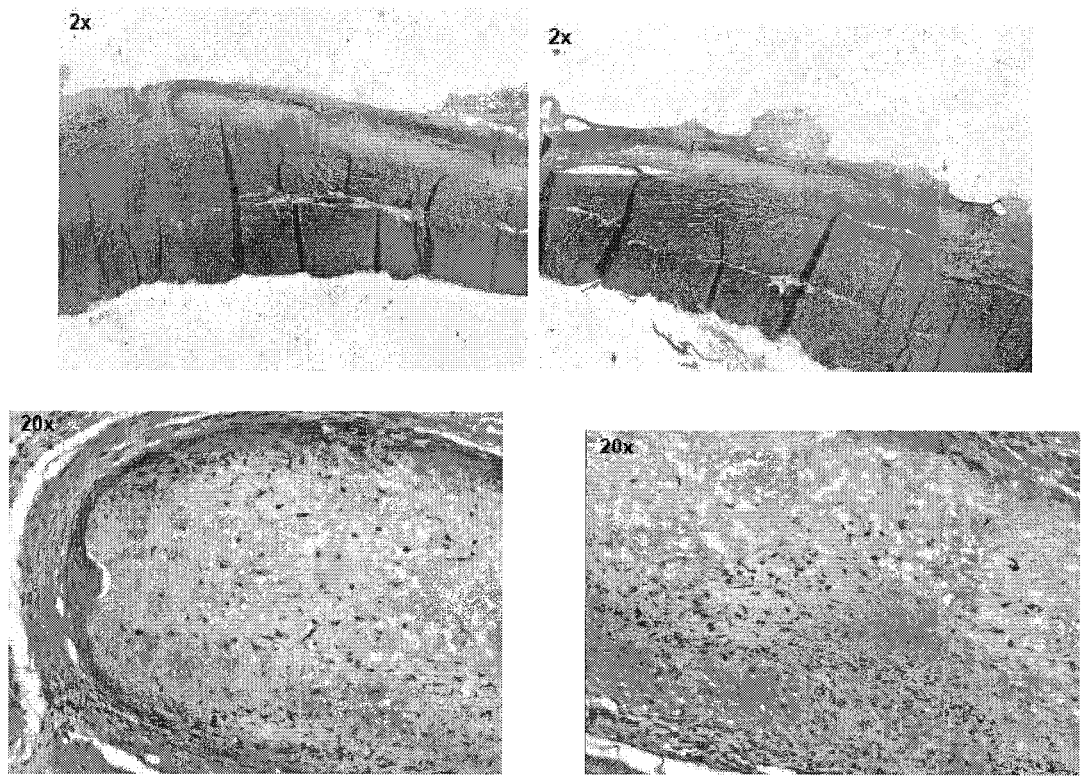
FIGS. 9A and 9B show photomicrographs (H&E stains) of two exemplary PEUU sections at two and four weeks, respectively, as described in the Examples below.
Figure 9B:
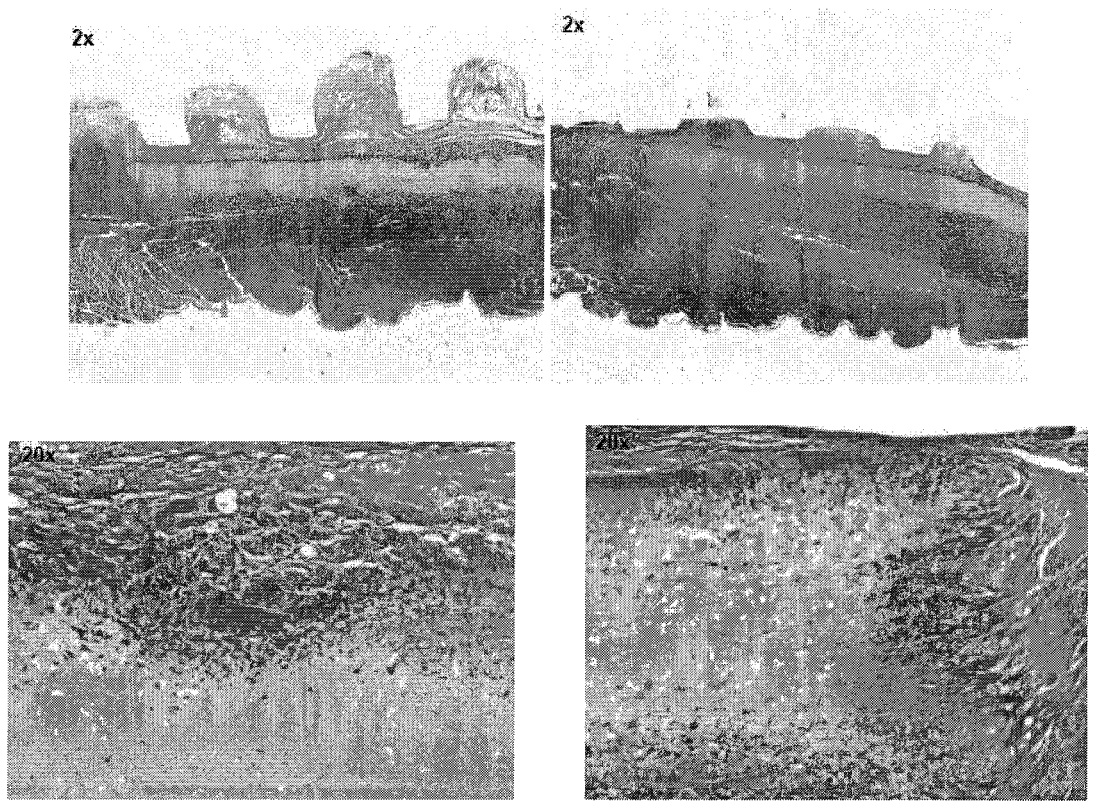
Figure 10A:
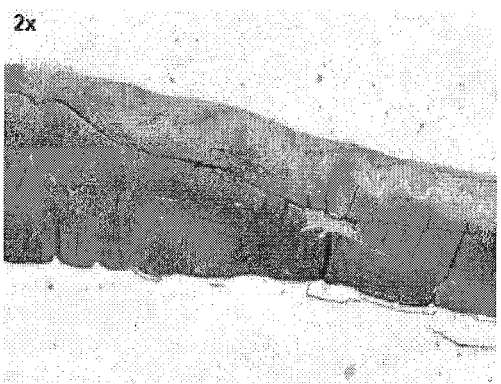
FIGS. 10A and 10B show photomicrographs (H&E stains) of two exemplary PEUU/dECM (50-50) sections at two and four weeks, respectively.
Figure 10A:
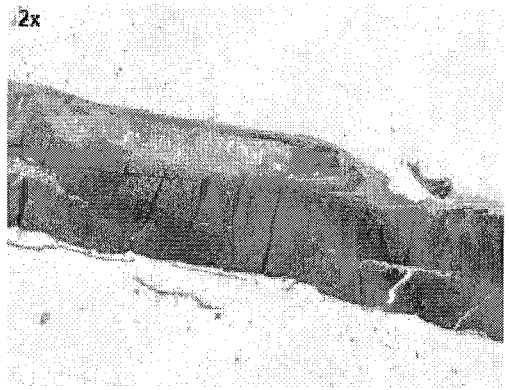
Figure 10A:
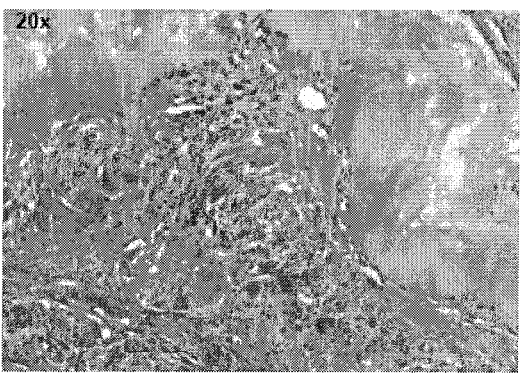
Figure 10A:
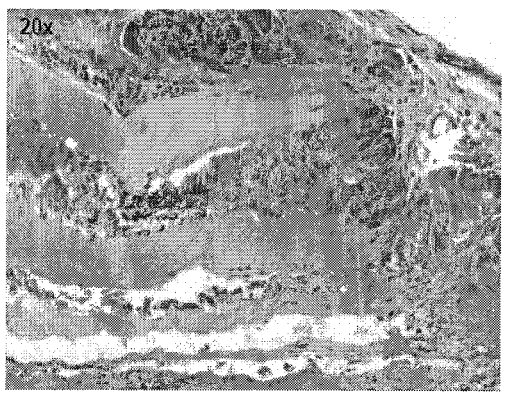
Figure 10B:
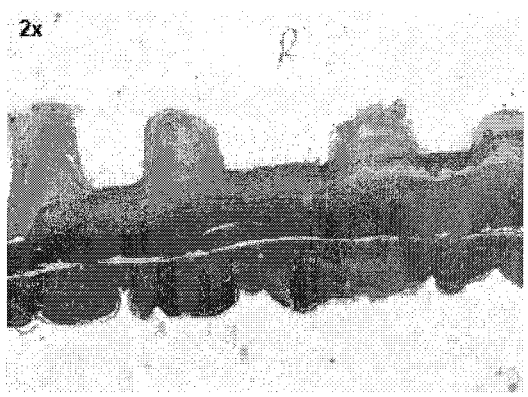
Figure 10B:
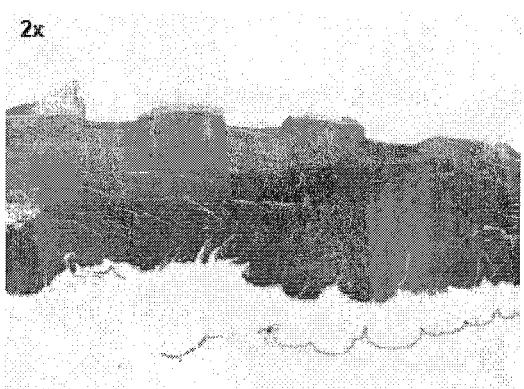
Figure 10B:
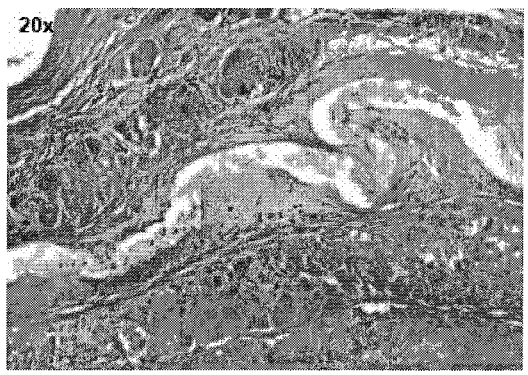
Figure 10B:
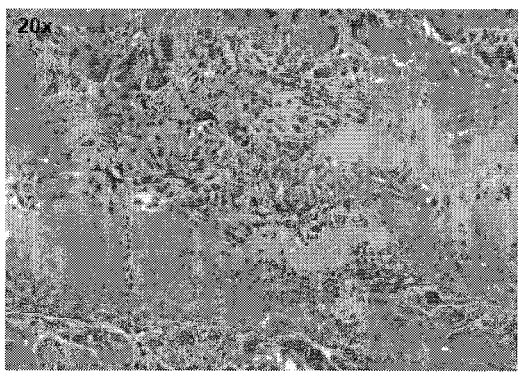

A PEUU/dECM hybrid scaffold (50/50) was prepared and tested in a partial thickness defect model in the rat (Valentin J E et al. J Bone Jt Surg Am 88 (2006), pp. 2673-2686; Brown B N et al. Biomaterials 30 (2008), pp. 1482-1491; Valentin J E et al. Biomaterials. 2010; 31(29):7475-7484). Briefly, a 1.0×1.0 cm lateral defect in muscle is used. Material (e.g., a biologic scaffold), replaces the outermost muscle layers (inner and outer obliques), while leaving in place the inner muscle layers (transversalis m.) and peritoneum. The material is attached using four sutures, one at each corner for demarcation and transfer of mechanical load. This model allows evaluation of biological integration as well as immune response to materials, and minimizes the effects of suturing materials. Scaffolds were prepared from electrospun PEUU, alone, as described above and 50-50 PEUU/dECM as described above. Scaffolds were implanted in a total of four rats, with one rat for each time point. FIG. 8 shows macroscopic images of both implants at two and four weeks post-implant. FIGS. 9A and 9B show photomicrographs (H&E stains) of two PEUU sections at two and four weeks, respectively. FIGS. 10A and 10B show photomicrographs (H&E stains) of two PEUU/dECM (50-50) sections at two and four weeks, respectively. In FIGS. 9A, 9B, 10A and 10B, the right and left images are from different areas of the implant in a single rat. Cellular infiltration and tissue remodeling appear significantly improved with the incorporation of the ECM gel into the scaffold.

A full-thickness animal model also was used for testing the scaffolds in rats. This tests the biomechanical properties of the scaffold, as the defect requires replacement of a higher amount of connective tissue than in the first, lateral partial defect model described above. A 1.0×2.5 cm defect is made on the animal's midline, with matched size replacement (~3-4 mm thick). The scaffold material replaces all muscle layers and peritoneum and is held in place using continuous sutures. This model facilitates evaluation of devices with focus on biomechanical properties. In this model a higher amount of connective tissue is replaced as compared to the lateral partial defect model.

Figure 11A:
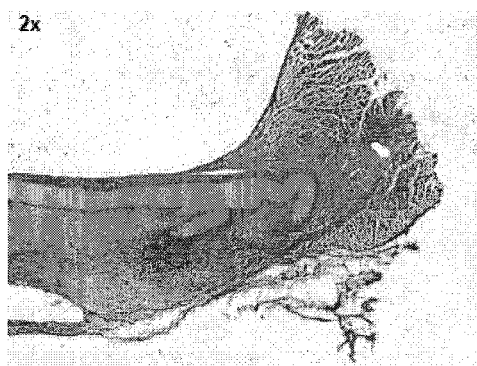
FIGS. 11A and 11B are photomicrographs showing Masson's Trichrome staining of rats' body wall treated with either a PEUU device or a device of acellular dECM at two and four weeks.
Figure 11A:
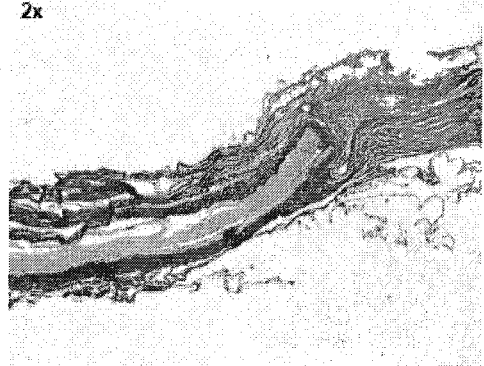
Figure 11A:
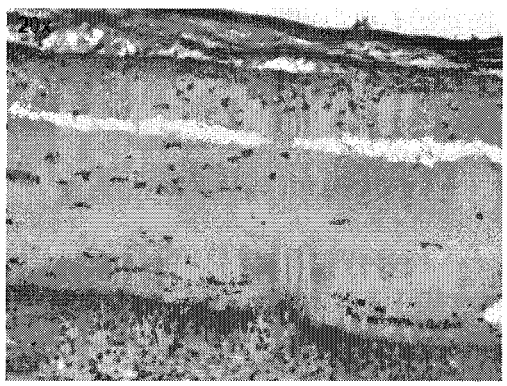
Figure 11A:
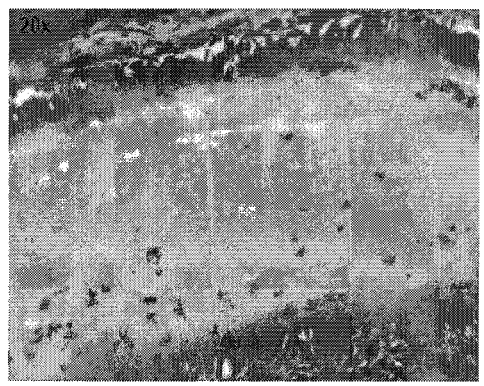
Figure 11B:
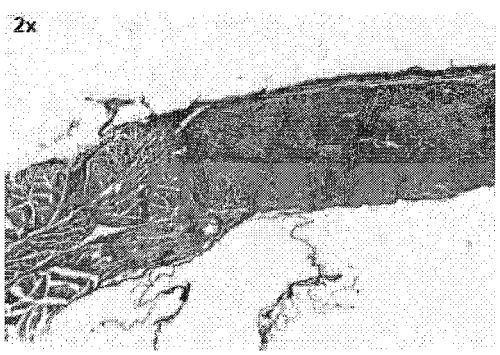
Figure 11B:
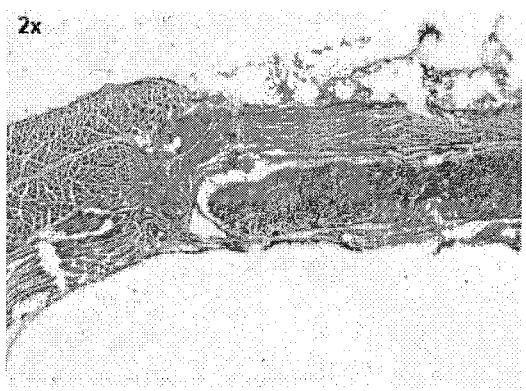
Figure 11B:
Figure 11B:
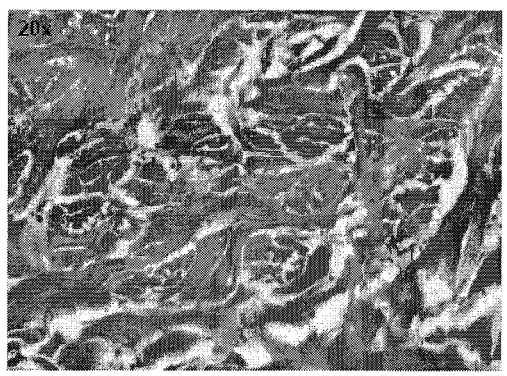
Figure 12A:
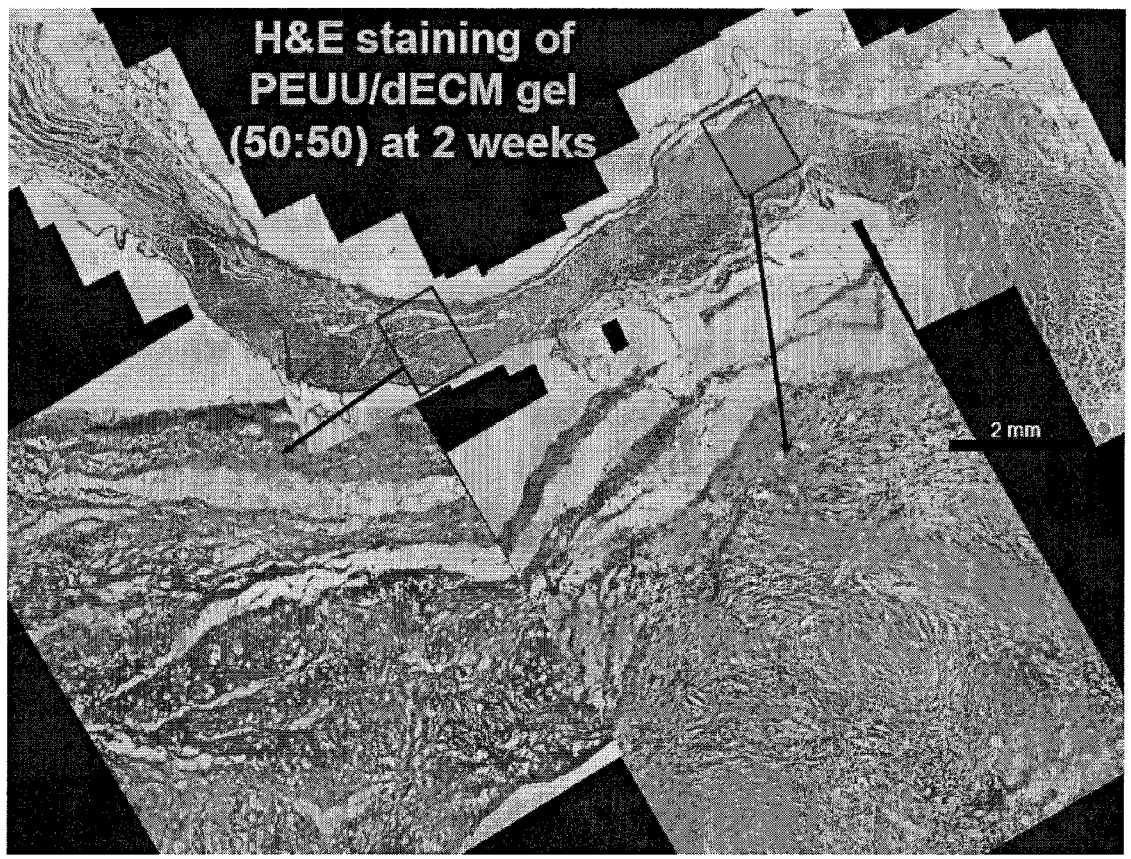
FIGS. 12A and 12B are photomicrographs showing an H&E stain of a rat abdominal wall cross-section repaired using a PEUU/dECM 50/50 hybrid scaffold. This shows good tissue infiltration.
Figure 12B:
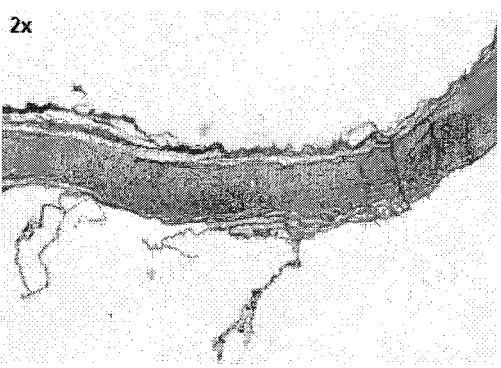
Figure 12B:
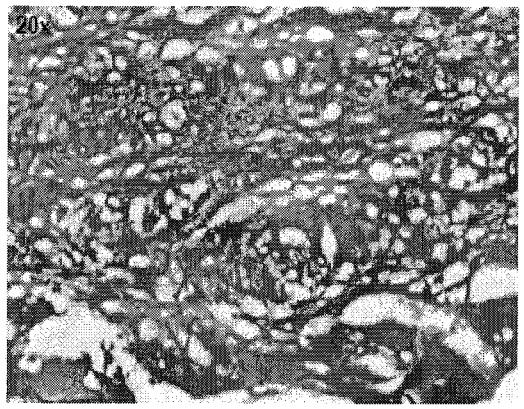
Figure 13:
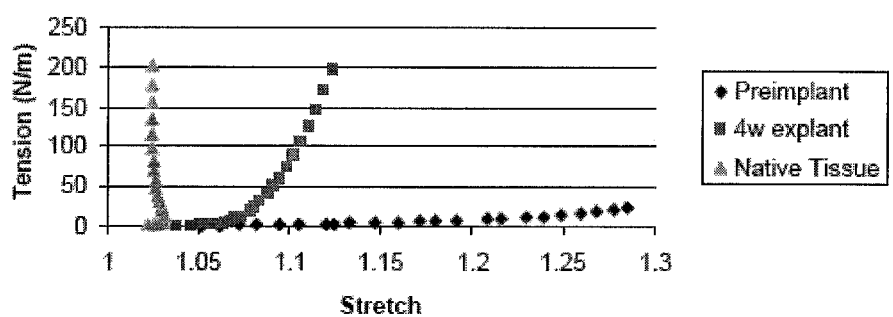
FIG. 13 provides graphs showing shows biaxial stress-stretch curves of native abdominal wall tissue and PEUU/dECM 50/50 hybrid scaffolds pre-implant and 4 weeks post-implant.
Figure 13:
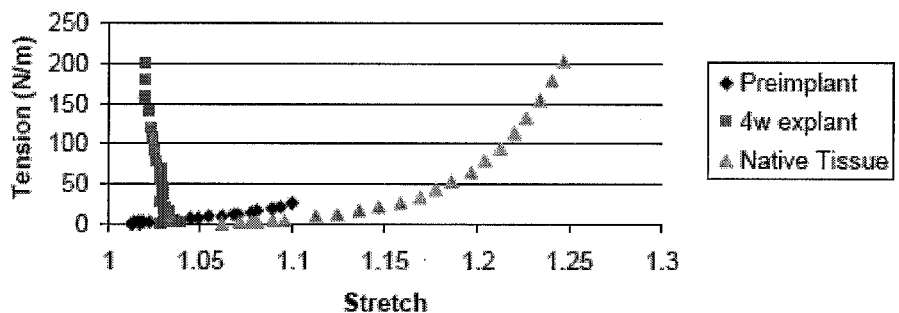

In this experiment, two rats were implanted with PEUU/dECM gel 50/50 hybrid scaffold. PEUU and dECM alone were implanted into rats as controls. At four weeks post implantation, vasculature was seen on the peritoneal side of the repair to some degree in all samples (PEUU, dECM or PEUU/dECM), but significantly more when the blended material was used. The PEUU/dECM expanded circumferentially (transversely), while no apparent change in longitudinal length was seen. FIGS. 11A and 11B show Masson's Trichrome staining of the rats body wall treated with either a PEUU device or a device of acellular dECM at two and four weeks. The PEUU group showed a very limited level of cellular infiltration into the device. The dECM-treated group showed a significantly level of cellular infiltration into the entire device. FIGS. 12A and 12B show photomicrographs of an H&E stain of a rat abdominal wall cross-section repaired using PEUU/dECM 50/50 hybrid scaffold. This shows good tissue infiltration. FIG. 13 shows biaxial stress-stretch curves of native abdominal wall tissue and for PEUU/dECM 50/50 hybrid scaffolds pre-implant and 4 weeks post-implant. The test curves were generated as described above.

Example 3

A patch material of PEUU/dECM 72/28 was prepared as described above. The PEUU was electrospun and the dECM gel was electrosprayed essentially as described above, and a dry polymer ratio of 72% PEUU and 28% dECM. 10 mL dermal ECM gel solution (10 mg/ml) was fed by a syringe pump at 1.5 mL/min into a sterilized capillary (1.2 mm inner diameter) charged at 7 kV and suspended 4 cm above the target mandrel (19 mm diameter). Concurrently, PEUU in hexafluoroisopropanol solution (12%, w/v) was fed at 20 mL/h from a capillary, charged at 12 kV and perpendicularly located 20 cm from the target mandrel. The mandrel was charged at −4 kV and rotated at 250 rpm (8 cm/s tangential velocity) while translating back and forth 8 cm along the x-axis at 0.15 cm/s. After processing, PEUU/gel solution hybrid was cut off from mandrel using a blade and then was immediately placed in an incubator at 37° C. After 2 h, dECM gel solution completely formed a solid gel and a PEUU/dECM 72/28 scaffold was obtained.

Figure 14A:
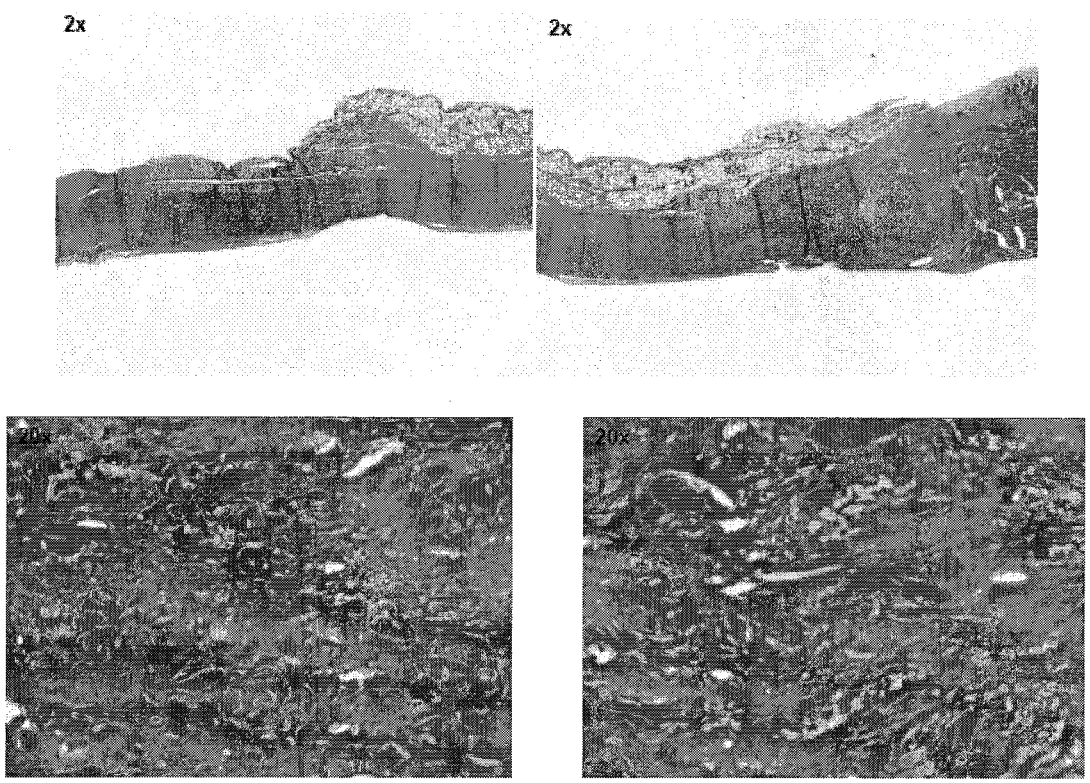
FIGS. 14A and 14B are photomicrographs of H&E stained cross sections of the PEUU/dECM 72/28 hybrid implant at two and four weeks, respectively, with left and right panels showing the microscopic results obtained in both animals implanted.
Figure 14B:
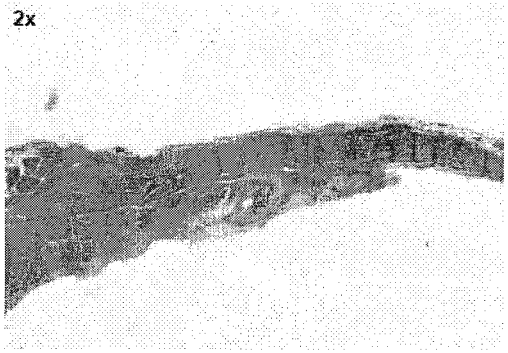
Figure 14B:
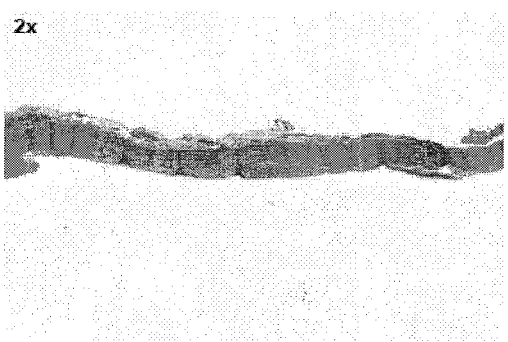
Figure 14B:
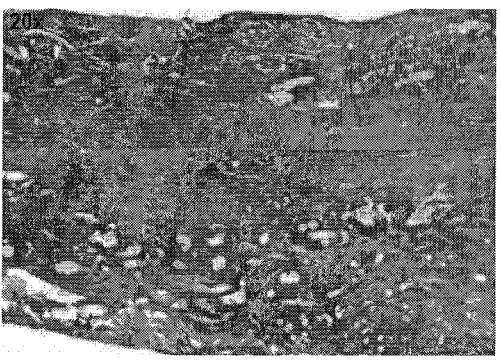
Figure 14B:
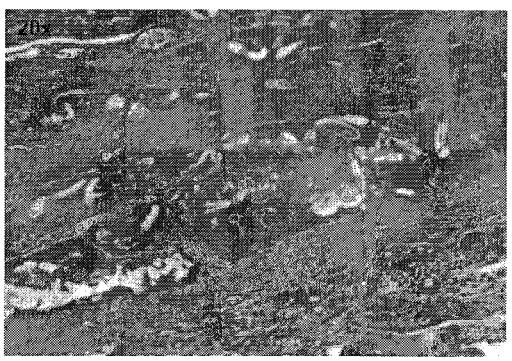
Figure 15:
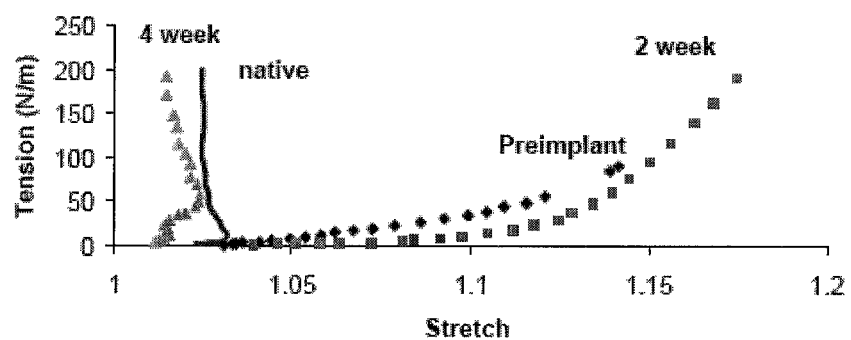
FIG. 15 shows biaxial stress-stretch curves of native abdominal wall tissue and for PEUU/dECM 50/50 hybrid scaffolds pre-implant, 2 and 4 weeks post-implant.
Figure 15:
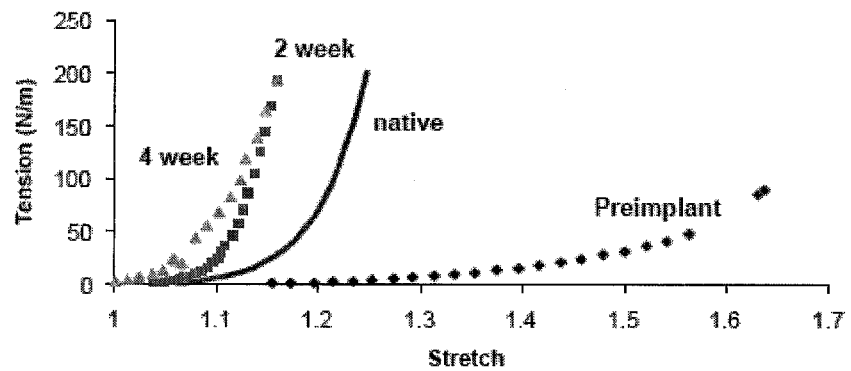

The patch was prepared as described above and implanted into two rats with an endpoint of 2 and 4 weeks. FIGS. 14A and 14B are photomicrographs of H&E stained cross sections of the PEUU/dECM 72/28 hybrid implant at two and four weeks, respectively, with left and right panels showing the microscopic results obtained in both animals implanted. FIG. 15 shows biaxial stress-stretch curves of native abdominal wall tissue and for PEUU/dECM 50/50 hybrid scaffolds pre-implant, 2 and 4 weeks post-implant.

Figure 16:
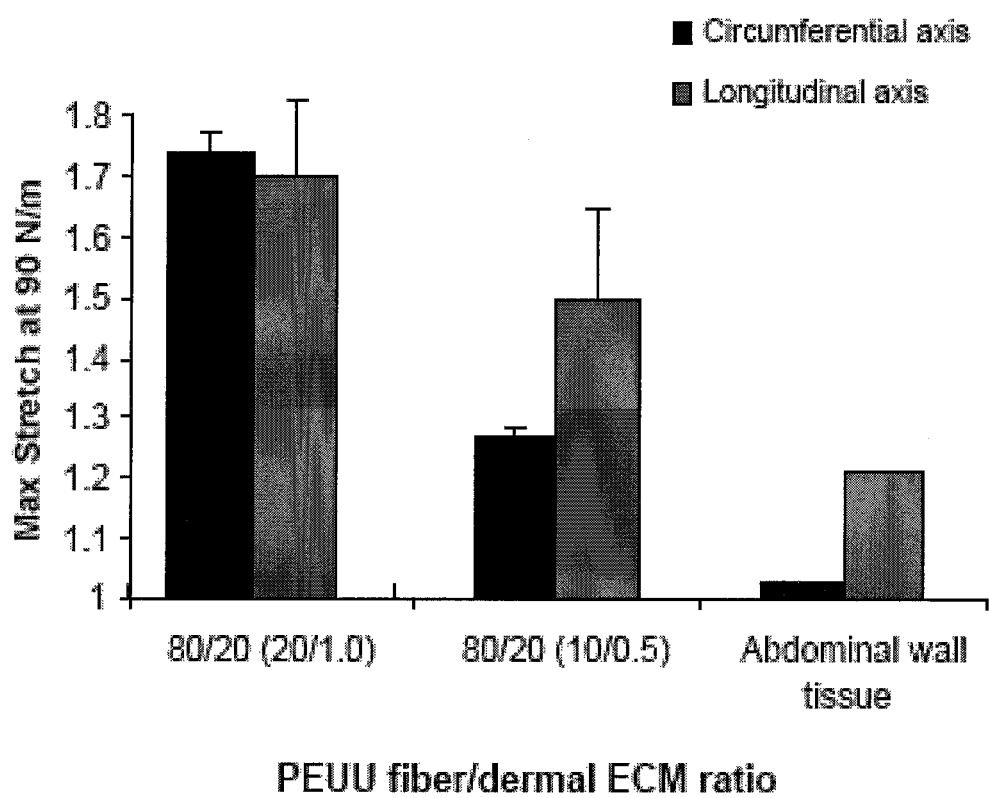
FIG. 16 is a graph showing the influence of processing parameters on mechanics of a pre-implantation patch. The numbers in brackets are the process conditions of the PEUU solution infusion rate (ml/h) to dermal ECM solution infuse rate (ml/min).

In sum, in the transition from the first to second generation materials, the amount of PEUU was increased with respect to the amount of dECM in the patch. In future trials, the flow rates of the PEUU and dECM during co-integration into the matrix may be altered to reduce solvent incorporation and change fiber diameter. Different compositions and flow rates at different times can produce different lamellar formulations that may prove beneficial. In a preliminary study, FIG. 16 shows the influence of processing parameters on mechanics of a pre-implantation patch. In FIG. 16, the number in bracket is the process condition of the PEUU solution infusion rate (ml/h) to dermal ECM solution infuse rate (ml/min). Slowing the polymer infusion rate generally leads to thinner fibers (higher density).

With respect PEUU/dECM [50/50] hybrid, there was a problem with reproducibility. There was a delamination effect in the sample used for partial defect repair, but not in sample used in full thickness model. The device was too weak (suture retention), high levels of cell infiltration, neotissue formation were seen in the PEUU/dECM gel biohybrid but not in PEUU alone, and a visible inflammatory response is seen, with multinucleated giant cells.

The materials having a higher ratio of PEUU to dECM (PEUU/dECM 72/28) exhibit improved strength as compared to the 50/50 hybrid, high levels of cellular infiltration, neotissue formation and remodeling to achieve mechanical properties comparable to native abdominal wall.

Even with these materials, though significant improvements over the 50/50 material, initial strength could be improved. Longer term results are planned, as is investigation of M1/M2 markers in vitro and in vivo.

Example 4

A severe abdominal wall defect due to laparotomy after abdominal compartment syndrome or severe abdominal injury remains a challenging problem for surgeons. Primary closure is difficult because of the risk of abdominal hyper pressure or intraabdominal infection. The standard treatment includes open treatment followed by secondary abdominal wall reconstruction. Many techniques utilizing autologous tissue or prosthetic materials have been applied to reconstruct full abdominal wall defects. But disadvantages for such two materials are complications, tissue adhesion, infections and hernia recurrence. Here, we designed a biohybrid composite material that offers both strength and bioactivity for optimal healing towards native tissue behavior. This material, which has top and bottom layers of polymer fibers and a middle layer of polymer fibers and extracellular matrix gel biohybrid, was fabricated using a sandwich technique, which includes wet electrospinning for the beginning and end of the processing, and gel electrospray/polymer electrospinning for the middle of processing. The resultant sandwich scaffold possessed attractive mechanical properties and anisotropic behavior mimicking native abdominal wall as well as good bioactivity for tissue ingrowth and remodeling. By creating a polymer-rich upper and lower surface the composite scaffold provides longer lasting structural elements that also provide good suturability. The ECM-rich interior provides a bioactive pathway for cell migration and accelerated healing. The fibers within the interior region provide structural connectivity to the rest of the scaffold and improve the mechanical properties. The biohybrid scaffold would find opportunities in the clinical applications for abdominal wall reconstruction, pelvic floor repair, breast reconstruction, as well as other soft tissue repairs.

The PEUU/dECM material (PEUU/dECM 72/28) described above was sandwiched between two layers of wet-electrospun PEUU. The material was prepared by continuous electrospinning on a mandrel of a PEUU solution and concurrently electrospraying first PBS (phosphate-buffered saline), followed by dECM solution described above, and followed by PBS.

In further detail, the PEUU, as described above, was electrospun and the dECM gel was electrosprayed essentially as described above, and a dry polymer ratio of 72% PEUU and 28% dECM. PEUU in hexafluoroisopropanol solution (12%, w/v) was fed at 20 mL/h from a capillary, charged at 12 kV and perpendicularly located 20 cm from the target mandrel. Concurrently, PBS and dECM was electrosprayed in the following order. First, PBS was fed by a syringe pump at 0.2 mL/min into a sterilized capillary (1.2 mm inner diameter) charged at 7 kV and suspended 4 cm above the target mandrel (19 mm diameter). Second, 10 mL dermal ECM gel solution (10 mg/ml) was fed by a syringe pump at 1.5 mL/min into a sterilized capillary (1.2 mm inner diameter) charged at 7 kV and suspended 4 cm above the target mandrel (19 mm diameter). Third, PBS was fed by a syringe pump at 0.2 mL/min into a sterilized capillary (1.2 mm inner diameter) charged at 7 kV and suspended 4 cm above the target mandrel (19 mm diameter). The mandrel was charged at −4 kV and rotated at 250 rpm (8 cm/s tangential velocity) while translating back and forth 8 cm along the x-axis at 0.15 cm/s. Three different electrospinning durations, 10 minutes, 20 minutes and 30 minutes were tested. After processing, the three-layer structure was cut off from the mandrel using a blade and then was immediately placed in an incubator at 37° C. After 2 h, dECM gel solution completely formed a solid gel and a hybrid composite structure was obtained, essentially as depicted in FIG. 2.

Figure 17:
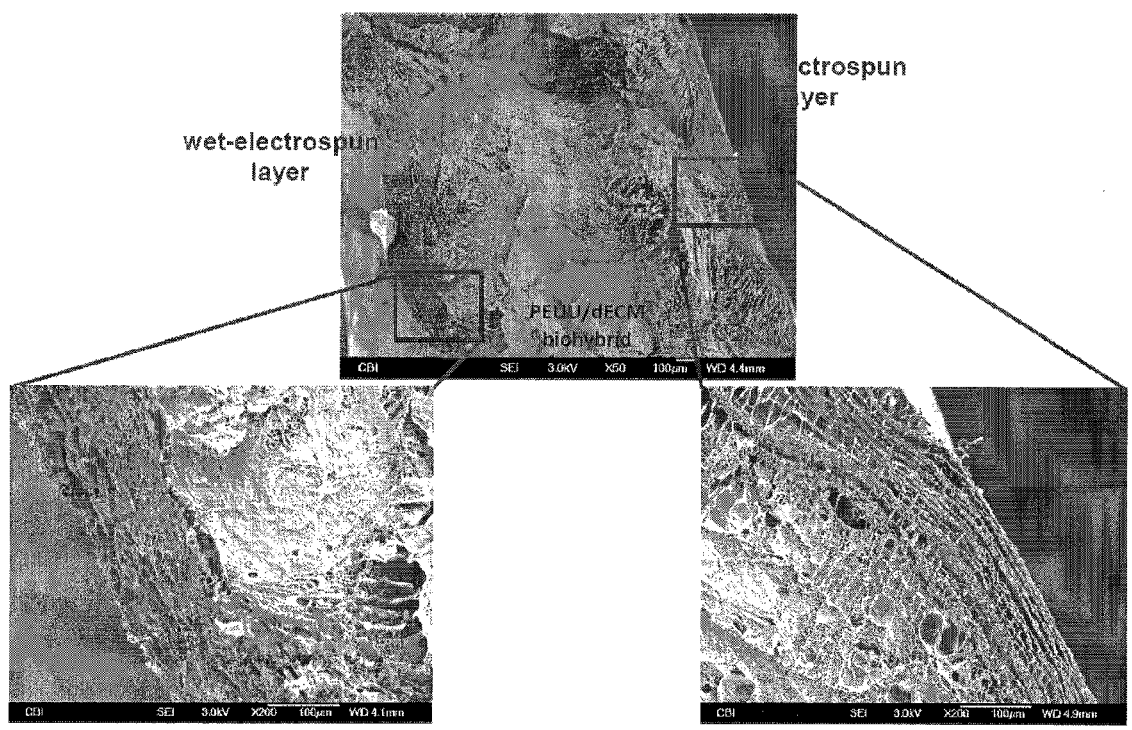
FIG. 17 are photomicrographs showing cross sections of the composite structure prepared by the method of Example 4.

FIG. 17 are photomicrographs showing cross sections of the composite structure prepared by this method.

Figure 18:
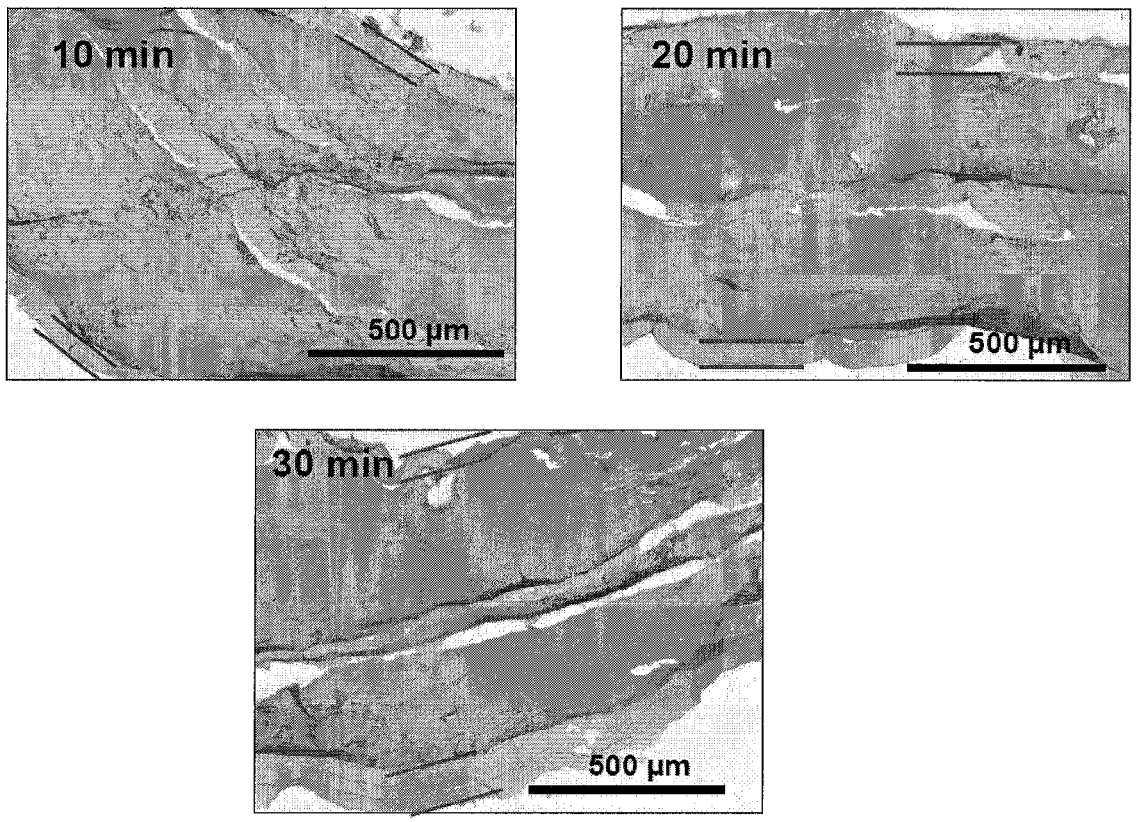
FIG. 18 are photomicrographs of Masson's trichrome stained cross-sections of the sandwiched sheets, for the three different electrospinning durations, as described in Example 4.

FIG. 18 are photomicrographs of Masson's trichrome stained cross-sections of the sandwiched sheets, for the three different electrospinning durations.

Figure 19:
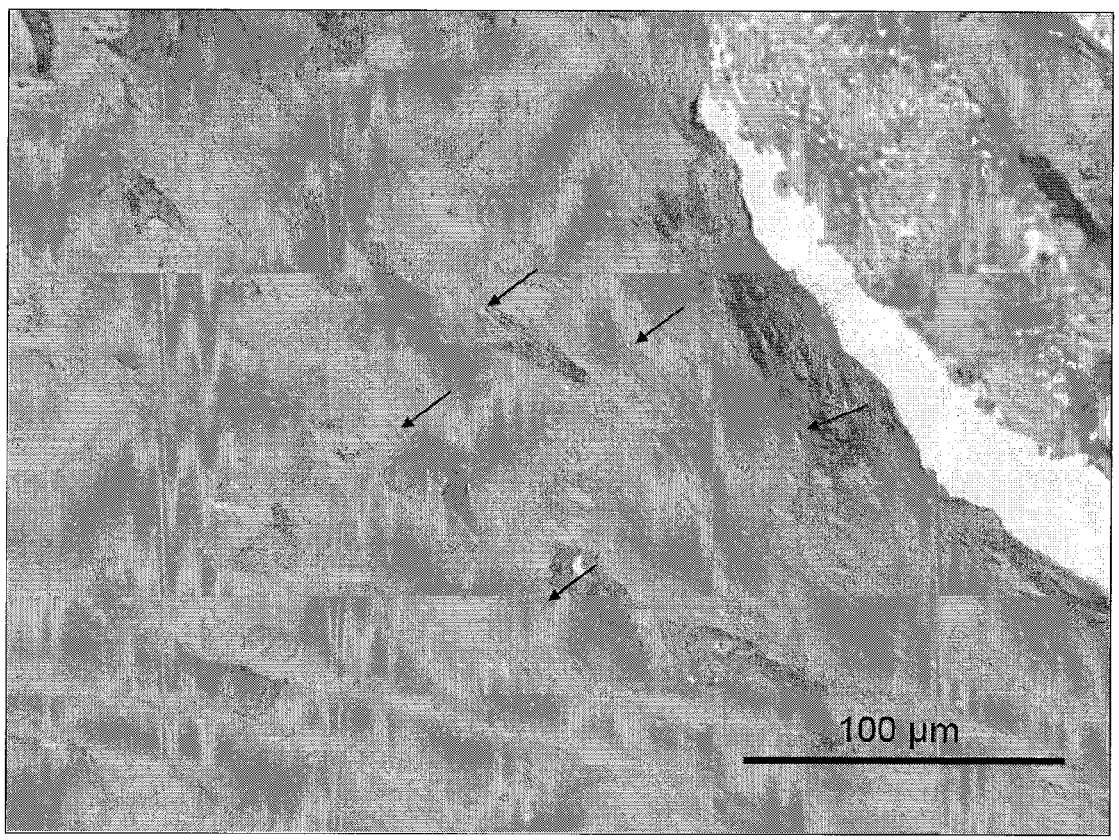
FIG. 19 is a photomicrograph of Masson's trichrome stained cross-sections of the sandwiched sheets (20 minute electrospinning duration), as described in Example 4.

FIG. 19 is a photomicrograph of Masson's trichrome stained cross-sections of the sandwiched sheets (20 minute electrospinning duration). This figure shows polymer fibers within the dECM gel region.

Figure 20A:
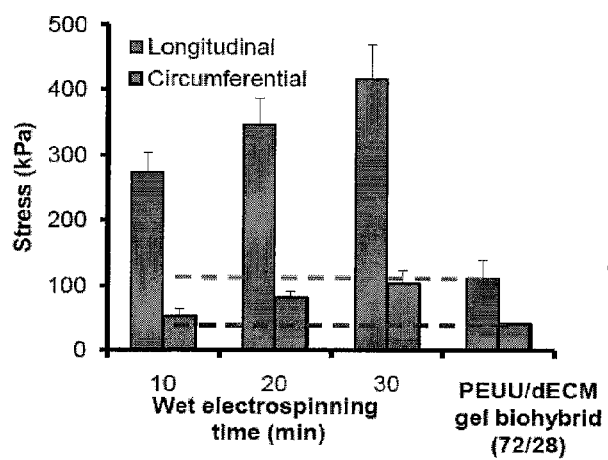
FIGS. 20A and 20B are graphs showing stress (FIG. 20A) and strain (FIG. 20B) values for the three composite structures prepared according to the methods described in Example 4, as compared to PEUU/dECM (72/28).
Figure 20B:
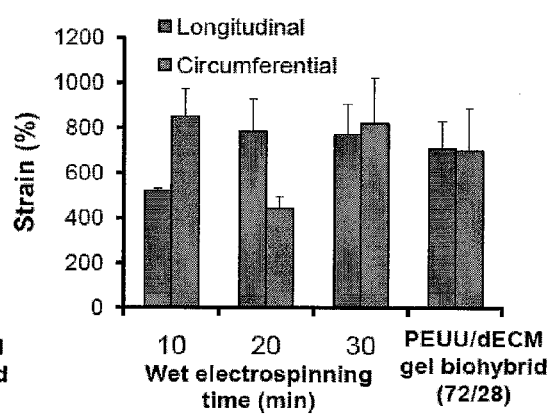

FIGS. 20A and 20B are graphs showing stress (FIG. 20B) and strain (FIG. 20B) values for the three composite structures prepared according to the methods described in the present example, as compared to PEUU/dECM (72/28) prepared as described above.

Figure 21:
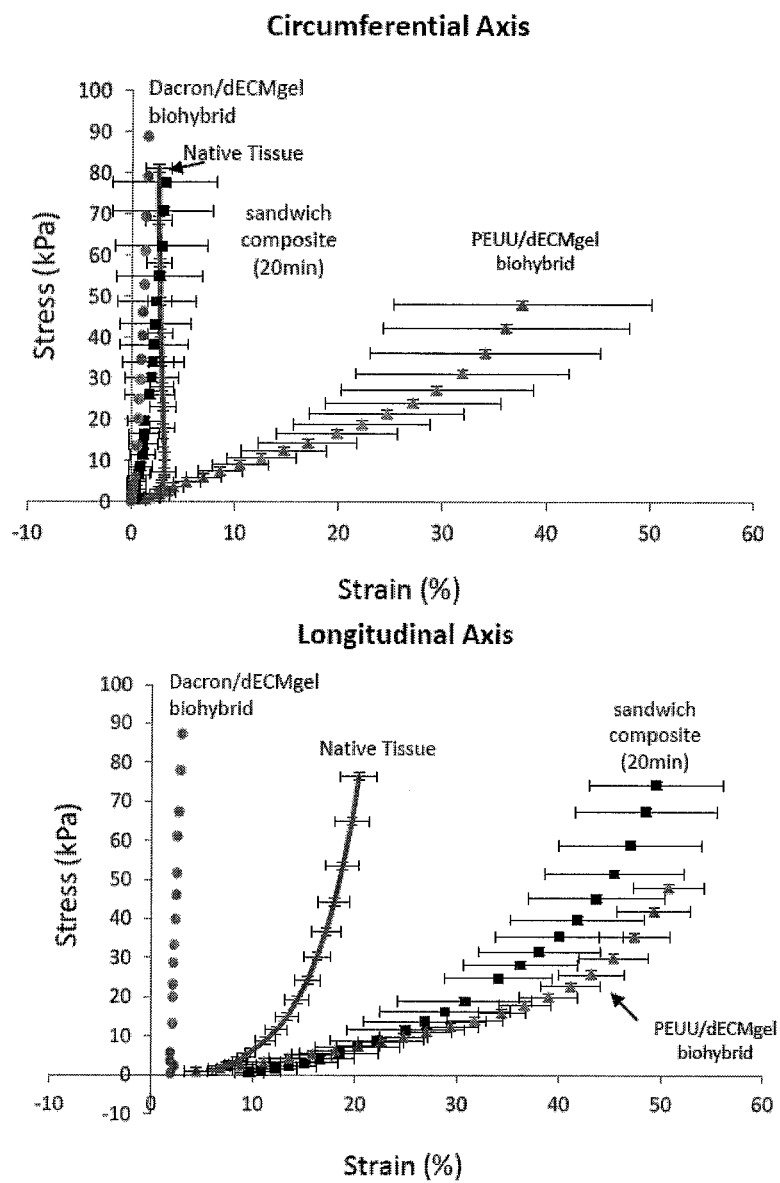
FIG. 21 are graphs providing comparisons of biaxial mechanical testing for the sandwich composite, PEUU/dECM material, native abdominal wall muscle tissue and a Dacron/dECM gel biohybrid, as described in Example 4.

FIG. 21 are graphs providing comparisons of biaxial mechanical testing for the sandwich composite (20 minutes), PEUU/dECM material, native abdominal wall muscle tissue (rat) and a Dacron/dECM gel biohybrid (non-degradable). Constructs were tested under equal biaxial tension. Of note the PEUU/dECM gel biohybrid (72:28) mechanically failed above 50 kPa.

Figure 22:
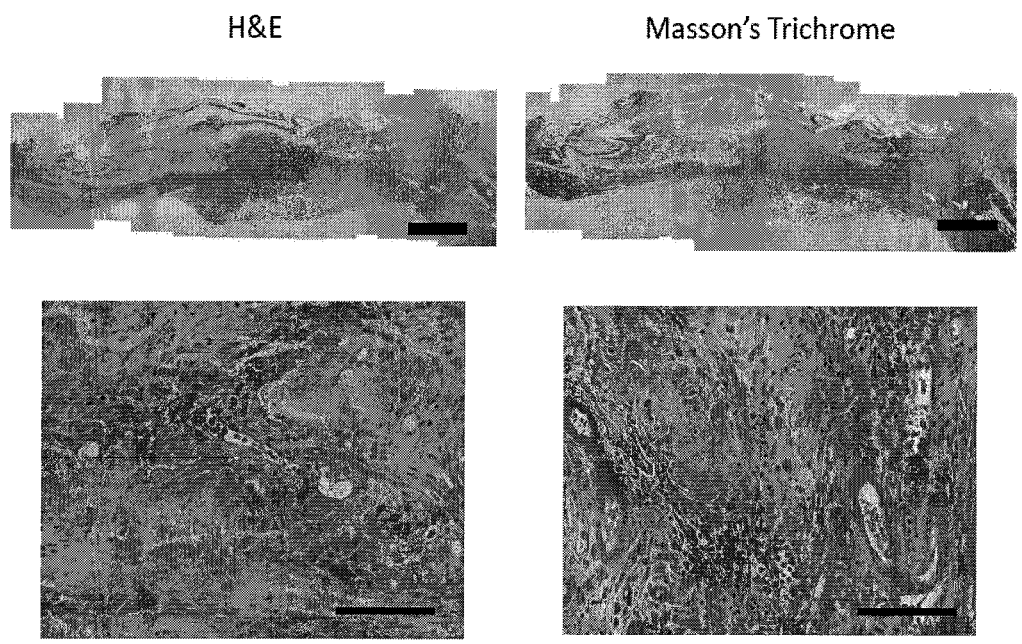
FIG. 22 are photomicrographs showing H&E and Masson's trichrome stains of that explanted tissue, as described in Example 4. Low magnification images (upper row, scale bar=1 mm) and high magnification images (bottom row, scale bar=100 μm).

The sandwich structure was implanted into rat abdominal wall essentially as described above (full thickness), along with a control PEUU/dECM (72/28). After three weeks, the material was explanted and analyzed. FIG. 22 provides photomicrographs showing H&E and Masson's trichrome stains of that explanted tissue.

Figure 23:
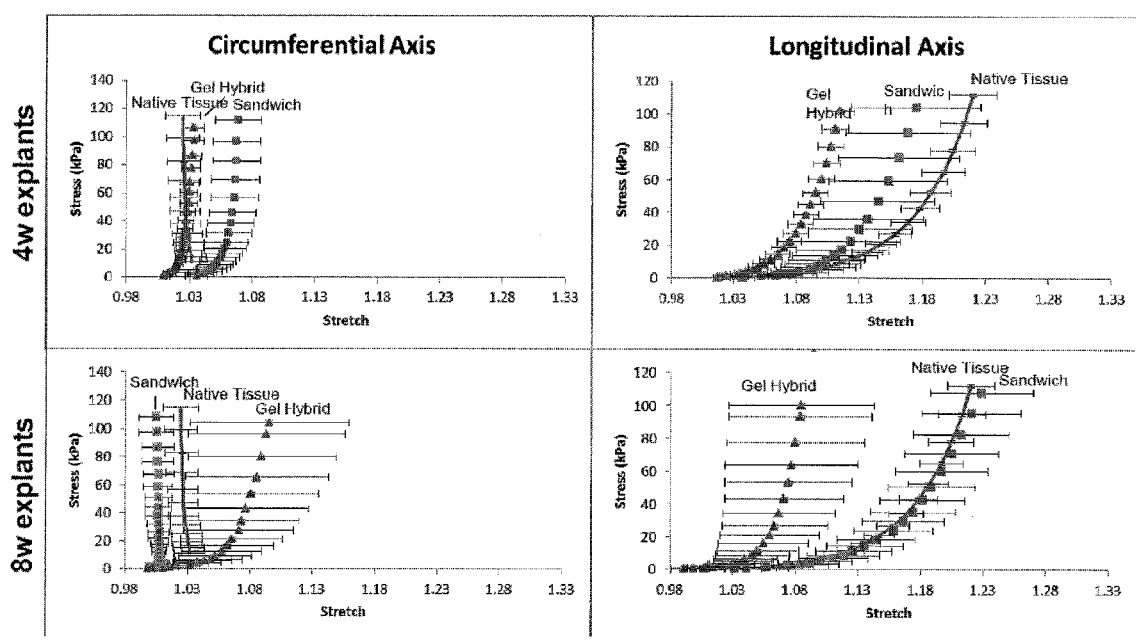
FIG. 23 are graphs providing comparisons of biaxial mechanical testing for the explanted sandwich composite, explanted PEUU/dECM (72:28) material, and native abdominal wall muscle tissue, as described in Example 4, at four and eight weeks post-implant.

FIG. 23 are graphs providing comparisons of biaxial mechanical testing for the explanted sandwich composite, explanted PEUU/dECM material, and native abdominal wall muscle tissue at four and eight weeks post-implant. The tissue explanted from the sandwich structure group shows excellent and unexpected similarity to native muscle tissue.

Figure 24:
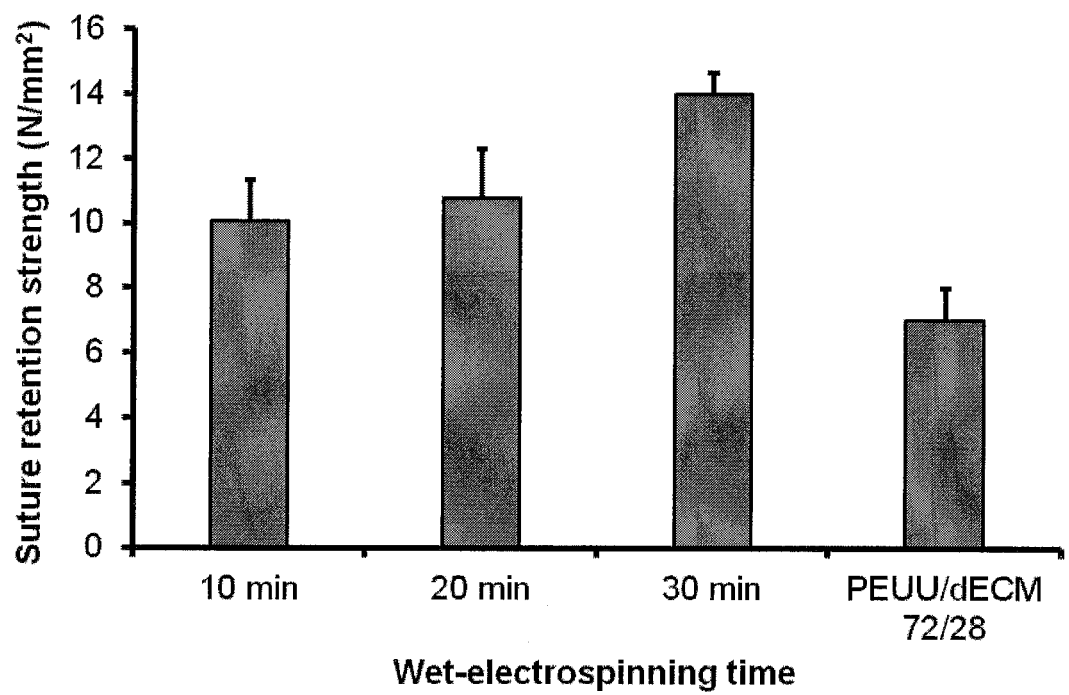
FIG. 24 is a graph showing suture retention strength of sandwich scaffold tuning by wet-electrospinning time, indicating the superiority of the sandwiched material as compared to the PEUU/dECM (72:28) material, as described in Example 4.

One of the goals of preparing the sandwiched composite structure is to improve suturability as compared to PEUU/dECM (72:28) material. Suture retention strength was therefore measured for the sandwiched material as compared to the PEUU/dECM (72:28) material. FIG. 24 is a graph showing suture retention strength of sandwich scaffold tuning by wet-electrospinning time, indicating the superiority of the sandwiched material as compared to the PEUU/dECM (72:28) material.

Having described this invention above, it will be understood to those of ordinary skill in the art that the same can be performed within a wide and equivalent range of conditions, formulations and other parameters without affecting the scope of the invention or any embodiment thereof.

This application is a National Stage of International Patent Application No. PCT/US2011/048071, filed Aug. 17, 2011, which claims the benefit of U.S. Provisional Patent Application No. 61/374,340, filed Aug. 17, 2010, each of which is herein incorporated by reference in its entirety.

We claim:

1. A method of making a biohybrid scaffold comprising:
   (a) concurrently or substantially concurrently:
      (1) electrospinning a biodegradable, biocompatible, elastomeric polymer composition onto a substrate; and
      (2) electrospraying an ECM-derived gel composition onto the substrate, thereby producing a first layer, wherein the ECM-derived gel composition is prepared by:
         (i) solubilizing decellularized tissue that has not been dialyzed by digestion with an acid protease, thereby producing a digest solution; and
         (ii) raising the pH of the digest solution to between 7.2 and 7.8.

2. The method of claim 1 wherein the substrate is a mandrel.

3. The method of claim 1 wherein the biodegradable, biocompatible elastomeric polymer comprises one or more of a poly(ester urethane)urea (PEUU), a poly(ether ester urethane)urea (PEEUU), a poly(ester carbonate)urethane urea (PECUU) and a poly(carbonate)urethane urea (PCUU).

4. The method of claim 3 in which the polymer comprises polycaprolactone.

5. The method of claim 4, in which the polycaprolactone has an Mw of 1000-5000.

6. The method of claim 4 in which the biodegradable, biocompatible elastomeric polymer comprises a copolymer of polycaprolactone, 1,4-diisocyanobutane and putrescine, wherein the Mw of polycaprolactone is ~2000.

7. The method of claim 1, in which the biodegradable, biocompatible elastomeric polymer composition is prepared from a polycaprolactone-polyethylene glycol-polycaprolactone triblock copolymer, an aliphatic diisocyanate and an aliphatic diamine.

8. The method of claim 7 in which the aliphatic diisocyanate is 1,4-diisocyanobutane and the aliphatic diamine is putrescine.

9. The method of claim 1, in which the polymer is prepared from an aliphatic diisocyanate and an aliphatic diamine.

10. The method of claim 9, in which the aliphatic diisocyanate is 1,4-diisocyanobutane and/or the diamine is putrescine.

11. The method of claim 1, in which the ECM-derived gel composition is prepared from dermal ECM, urinary bladder ECM and/or small intestine ECM.

12. The method of claim 1, in which the scaffold comprises >50% wt of the biodegradable, biocompatible elastomeric polymer.

13. The method of claim 1, further comprising
   (b) concurrently or substantially concurrently:
      (1) electrospinning a biodegradable, biocompatible, elastomeric polymer and
      (2) spraying a liquid, an aqueous liquid, or a liquid selected from the group consisting of water, a physiological salt solution, a buffer solution, a mammalian blood product and cell culture medium, onto the first layer, thereby producing a second layer.

14. A method of making a biohybrid scaffold comprising:
   (a) concurrently or substantially concurrently:
      (1) electrospinning a biodegradable, biocompatible, elastomeric polymer onto a substrate and
      (2) spraying a liquid, an aqueous liquid, or a liquid selected from the group consisting of water, a physiological salt solution, a buffer solution, a mammalian blood product and cell culture medium, onto the substrate, thereby producing a first layer; and
   (b) concurrently or substantially concurrently:
      (1) electrospinning a biodegradable, biocompatible, elastomeric polymer composition onto the substrate and
      (2) electrospraying an ECM-derived gel composition onto the first layer, thereby producing a second layer, wherein the ECM-derived gel composition is prepared by:
         (i) solubilizing decellularized tissue that has not been dialyzed by digestion with an acid protease, thereby producing a digest solution; and
         (ii) raising the pH of the digest solution to between 7.2 and 7.8.

15. The method of claim 14, further comprising:
   (c) concurrently or substantially concurrently:
      (1) electrospinning a biodegradable, biocompatible, elastomeric polymer and
      (2) spraying a liquid, an aqueous liquid, or a liquid selected from the group consisting of water, a physiological salt solution, a buffer solution, a mammalian blood product and cell culture medium, onto the second layer, thereby producing a third layer.

16. The method of claim 14, in which the biodegradable elastomeric polymer of step (a) and/or step (b) is one or more of a poly(ester urethane) urea (PEUU), a poly(ether ester urethane)urea PEEUU), a poly(ester carbonate)urethane urea (PECUU) and a poly(carbonate)urethane urea (PCUU).

* * * * *